United States Patent
An et al.

(10) Patent No.: US 10,918,858 B2
(45) Date of Patent: Feb. 16, 2021

(54) CARDIAC VOLUME SENSING VIA AN IMPLANTABLE MEDICAL DEVICE IN SUPPORT OF CARDIAC RESYNCHRONIZATION THERAPY

(71) Applicant: CARDIAC PACEMAKERS, INC., St. Paul, MN (US)

(72) Inventors: Qi An, Blaine, MN (US); Jeffrey E. Stahmann, Ramsey, MN (US); Yinghong Yu, Shoreview, MN (US); Pramodsingh Hirasingh Thakur, Woodbury, MN (US); Michael J. Kane, St. Paul, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 27 days.

(21) Appl. No.: 15/654,261

(22) Filed: Jul. 19, 2017

(65) Prior Publication Data
US 2018/0021570 A1 Jan. 25, 2018

Related U.S. Application Data

(60) Provisional application No. 62/364,637, filed on Jul. 20, 2016.

(51) Int. Cl.
*A61N 1/362* (2006.01)
*A61N 1/05* (2006.01)
(Continued)

(52) U.S. Cl.
CPC .......... *A61N 1/0587* (2013.01); *A61B 5/0031* (2013.01); *A61N 1/059* (2013.01);
(Continued)

(58) Field of Classification Search
None
See application file for complete search history.

(56) References Cited

U.S. PATENT DOCUMENTS 4,535,774 A * 8/1985 Olson ................ A61N 1/36521
607/24
4,686,987 A * 8/1987 Salo .................... A61N 1/36521
607/24
(Continued)

FOREIGN PATENT DOCUMENTS

EP 2280759 B1 5/2015
WO 2003051457 A1 6/2003
(Continued)

OTHER PUBLICATIONS

Ginks et al., "Relationship between intracardiac impedance and left ventricular contractility in patients undergoing cardiac resynchronization", Europace, vol. 13, 984-991, 2001.
(Continued)

*Primary Examiner* — Erica S Lee
(74) *Attorney, Agent, or Firm* — Seager, Tufte & Wickhem LLP.

(57) ABSTRACT

An Implantable Medical Device (IMD) configured to be implantable in a ventricle of a patient's heart may include a housing, a first electrode secured relative to the housing, a second electrode secured relative to the housing, the second electrode spaced from the first electrode, and circuitry in the housing operatively coupled to the first electrode and the second electrode. The circuitry may be configured to identify a measure of impedance between the first electrode and the second electrode at each of a plurality of times during a cardiac cycle. Each measure of impedance may represent a measure of volume of the ventricle in which the IMD is implanted. In some cases, the circuitry may generate a pacing pulse, the timing of which is based at least in part on
(Continued)

the measure of volume of the ventricle at two or more of the plurality of times during the cardiac cycle.

20 Claims, 14 Drawing Sheets

(51) Int. Cl.
*A61N 1/375* (2006.01)
*A61B 5/00* (2006.01)
*A61N 1/39* (2006.01)

(52) U.S. Cl.
CPC .......... *A61N 1/362* (2013.01); *A61N 1/3752* (2013.01); *A61N 1/3756* (2013.01); *A61N 1/37512* (2017.08); *A61N 1/3962* (2013.01)

(56) References Cited

U.S. PATENT DOCUMENTS

| | | | |
|---|---|---|---|
| 5,417,715 A * | 5/1995 | Noren | A61N 1/36521 607/24 |
| 6,314,323 B1 | 11/2001 | Ekwall | |
| 7,142,917 B2 | 11/2006 | Fukui | |
| 7,212,861 B1 | 5/2007 | Park et al. | |
| 7,286,875 B1 | 10/2007 | Park et al. | |
| 7,580,746 B2 | 8/2009 | Gilkerson et al. | |
| 7,596,412 B1 | 9/2009 | Kroll | |
| 7,630,763 B2 | 12/2009 | Kwok et al. | |
| 7,676,266 B1 | 3/2010 | Kroll | |
| 7,702,389 B2 | 4/2010 | Czygan et al. | |
| 7,702,392 B2 | 4/2010 | Echt et al. | |
| 8,306,621 B2 | 11/2012 | Kim et al. | |
| 8,478,400 B2 | 7/2013 | Hettrick et al. | |
| 8,521,265 B2 | 8/2013 | Vollkron et al. | |
| 8,527,068 B2 | 9/2013 | Ostroff | |
| 8,831,721 B2 | 9/2014 | Hettrick et al. | |
| 8,843,198 B2 | 9/2014 | Lian et al. | |
| 9,078,627 B2 * | 7/2015 | Razavi | A61B 5/053 |
| 9,174,062 B2 | 11/2015 | Stadler et al. | |
| 9,199,086 B2 | 12/2015 | Zielinski et al. | |
| 9,265,954 B2 | 2/2016 | Ghosh | |
| 9,265,955 B2 | 2/2016 | Ghosh | |
| 10,195,441 B2 * | 2/2019 | Kaiser | A61N 1/36585 |
| 2001/0012953 A1 | 8/2001 | Molin et al. | |
| 2001/0021864 A1 | 9/2001 | Molin | |
| 2001/0031995 A1 | 10/2001 | Molin | |
| 2001/0034540 A1 | 10/2001 | Molin | |
| 2001/0049543 A1 | 12/2001 | Kroll | |
| 2002/0087089 A1 | 7/2002 | Ben-Haim | |
| 2003/0204212 A1 | 10/2003 | Burnes et al. | |
| 2004/0172077 A1 | 9/2004 | Chinchoy | |
| 2005/0038481 A1 | 2/2005 | Chinchoy et al. | |
| 2005/0182447 A1 | 8/2005 | Schecter | |
| 2006/0271119 A1 * | 11/2006 | Ni | A61N 1/3627 607/9 |
| 2007/0055170 A1 | 3/2007 | Lippert et al. | |
| 2007/0060961 A1 | 3/2007 | Echt et al. | |
| 2007/0239219 A1 * | 10/2007 | Salo | A61N 1/3627 607/18 |
| 2008/0103744 A1 * | 5/2008 | Rom | G16H 50/50 703/11 |
| 2008/0195167 A1 | 8/2008 | Ryan | |
| 2008/0269816 A1 | 10/2008 | Prakash et al. | |
| 2010/0069768 A1 | 3/2010 | Min et al. | |
| 2010/0113945 A1 | 5/2010 | Ryan | |
| 2010/0198288 A1 | 8/2010 | Ostroff | |
| 2011/0160787 A1 | 6/2011 | Greenhut et al. | |
| 2012/0136406 A1 * | 5/2012 | Min | A61N 1/3627 607/25 |
| 2012/0165692 A1 | 6/2012 | Hollmark et al. | |
| 2013/0079839 A1 | 3/2013 | Lian et al. | |
| 2013/0116529 A1 * | 5/2013 | Min | A61B 5/0006 600/375 |
| 2014/0277240 A1 | 9/2014 | Maskara et al. | |
| 2015/0202443 A1 | 7/2015 | Zielinski et al. | |
| 2015/0367135 A1 * | 12/2015 | Whittington | A61N 1/3962 607/4 |
| 2016/0059024 A1 | 3/2016 | Stahmann et al. | |
| 2016/0067490 A1 | 3/2016 | Carney et al. | |
| 2016/0310723 A1 * | 10/2016 | Eggen | A61N 1/3756 |

FOREIGN PATENT DOCUMENTS

| | | |
|---|---|---|
| WO | 2004078254 A2 | 9/2004 |
| WO | 2005018740 A1 | 3/2005 |
| WO | 2007033094 A2 | 10/2007 |
| WO | 2009131768 A1 | 10/2009 |
| WO | 2010088687 A1 | 8/2010 |
| WO | 2014178035 A1 | 11/2014 |

OTHER PUBLICATIONS

MPVS Ultra, "Complete PV Loop Analysis", Pressure-Volume Loop Systems, Millar, downloaded Nov. 2017.
Roest et al., "Prediction of long-term outcome of cardiac resynchronization therapy by acute pressure-volume loop mesurments", European Journal of Heart Failure, 15, 299-307, 2013.

* cited by examiner

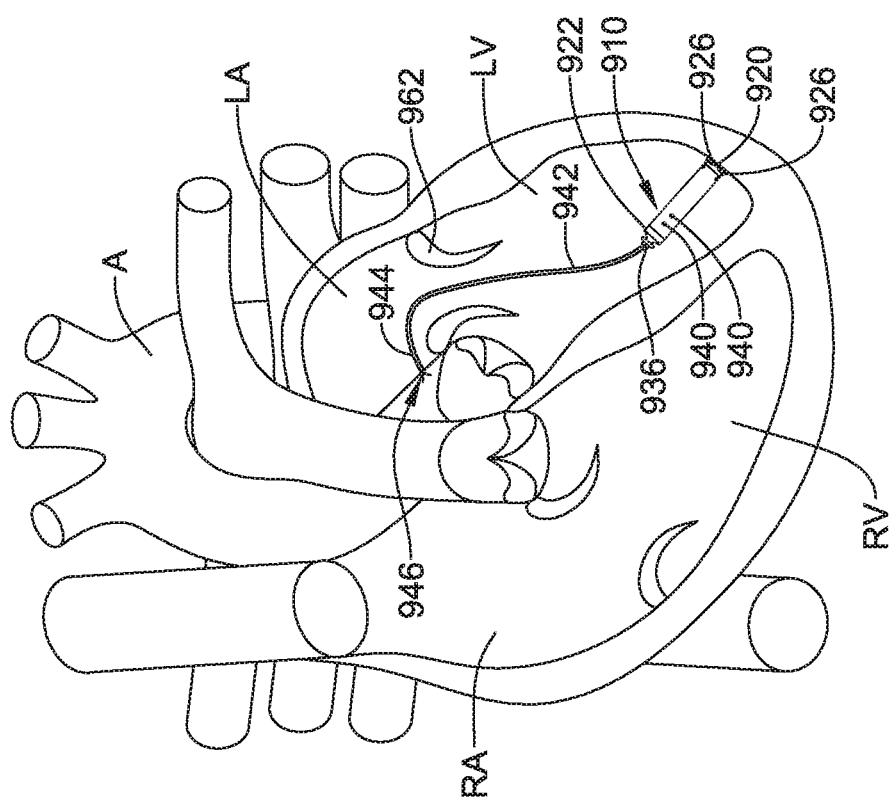

CARDIAC VOLUME SENSING VIA AN IMPLANTABLE MEDICAL DEVICE IN SUPPORT OF CARDIAC RESYNCHRONIZATION THERAPY

CROSS REFERENCE TO RELATED APPLICATIONS

This application claims the benefit of U.S. Provisional Patent Application Ser. No. 62/364,637 filed on Jul. 20, 2016, the disclosure of which is incorporated herein by reference

TECHNICAL FIELD

The present disclosure generally relates to implantable medical devices and more particularly to implantable medical devices for treating heart conditions.

BACKGROUND

Medical devices are often used to treat patients suffering from various heart conditions. These heart conditions may lead to rapid, irregular, and/or inefficient heart contractions. To help alleviate some of these conditions, various devices (e.g., pacemakers, defibrillators, etc.) can be implanted in a patient's body. Such devices often monitor and/or provide therapy, such as electrical stimulation therapy, to the patient's heart to help the heart operate in a more normal, efficient and/or safe manner. In some cases, a patient may have multiple implanted devices that cooperate to monitor and/or provide therapy to the patient's heart.

SUMMARY

The present disclosure generally relates to implantable medical devices (IMDs) and more particularly to implantable leadless medical devices.

In a first example of the disclosure, a leadless cardiac pacemaker (LCP) configured to be implantable in a ventricle of a patient's heart may comprise a housing, a first electrode secured relative to the housing and exposed to the environment outside of the housing, a second electrode secured relative to the housing and exposed to the environment outside of the housing, the second electrode spaced from the first electrode, and circuitry in the housing operatively coupled to the first electrode and the second electrode. The circuitry may be configured to identify a measure of impedance between the first electrode and the second electrode at each of a plurality of times during a cardiac cycle. Each measure of impedance may represent a measure of volume of the ventricle in which the LCP is implanted. The circuitry may further generate a pacing pulse, the timing of which is based at least in part on the measure of volume of the ventricle at two or more of the plurality of times during the cardiac cycle.

Alternatively or additionally to any of the examples above, in another example, the housing may include a rigid body and a tail, and the second electrode may be secured to the tail.

Alternatively or additionally to any of the examples above, in another example, the rigid body may have a first fixation element for fixing the rigid body to a first location in the ventricle, and the tail may include a second fixation element for fixing the tail to a second location.

Alternatively or additionally to any of the examples above, in another example, the second location may be in the ventricle.

Alternatively or additionally to any of the examples above, in another example, the second location may be in the atrium.

Alternatively or additionally to any of the examples above, in another example, the tail may include two or more electrodes, and the circuitry may be configured to select one of the two or more electrodes of the tail to be the second electrode.

Alternatively or additionally to any of the examples above, in another example, the housing may comprise three or more electrodes, and the circuitry may be configured to select one of the three or more electrode as the second electrode.

Alternatively or additionally to any of the examples above, in another example, the LCP may further comprise a third electrode secured relative to the housing and exposed to the environment outside of the housing and a fourth electrode secured relative to the housing and exposed to the environment outside of the housing. The fourth electrode may be spaced from the fourth electrode. The circuitry may be configured to apply an impedance current between third electrode and the fourth electrode, and the circuitry may be configured to sense a voltage between the first electrode and the second electrode to identify the measure of impedance between the first electrode and the second electrode.

Alternatively or additionally to any of the examples above, in another example, the circuitry may be configured to sense a voltage between the first electrode and the second electrode to identify the measure of impedance between the first electrode and the second electrode, when an impedance current is applied by a remote device.

Alternatively or additionally to any of the examples above, in another example, the circuitry may be configured to identify a contraction of the atrium of the patient's heart during the cardiac cycle based at least in part on the impedances taken at the plurality of times during the cardiac cycle. The timing of the pacing pulse may be based at least in part on the identified contraction of the atrium.

Alternatively or additionally to any of the examples above, in another example, the circuitry may be configured to communicate the measure of impedance between the first electrode and the second electrode at each of the plurality of times during the cardiac cycle to a remote device.

Alternatively or additionally to any of the examples above, in another example, the circuitry may be configured to receive processed information from the remote device that is a result of the remote device processing the measure of impedance between the first electrode and the second electrode at each of the plurality of times during the cardiac cycle.

Alternatively or additionally to any of the examples above, in another example, the timing of the pacing pulse may be based at least in part on the processed information from the remote device.

In another example, a leadless cardiac pacemaker (LCP) configured to be implantable in a ventricle of a patient's heart may comprise a housing comprising rigid body and a tail, a first electrode secured relative to the rigid body and exposed to the environment outside of the housing, a second electrode secured relative to the tail and exposed to the environment outside of the tail, the second electrode is spaced from the first electrode, and circuitry in the housing operatively coupled to the first electrode and the second electrode. The circuitry may be configured to identify a measure of impedance between the first electrode and the second electrode at each of a plurality of times during a cardiac cycle, wherein each measure of impedance represents a measure of volume of the ventricle in which the LCP is implanted and to store the measure of impedance between the first electrode and the second electrode at each of a plurality of times during a cardiac cycle in a memory.

Alternatively or additionally to any of the examples above, in another example, the circuitry may be further configured to identify a change from a passive filling to an active filling of the ventricle in which the LCP is implanted by detecting a change in slope of the plurality of impedances.

Alternatively or additionally to any of the examples above, in another example, the plurality of times may include\ at least one time corresponding to an end-systolic time point and at least one time corresponding to an end-diastolic time point, and a difference of an impedance determined at the end diastolic time point and an impedance determined at the end-systolic time point is a measure of a stroke volume of the ventricle in which the LCP is implanted.

Alternatively or additionally to any of the examples above, in another example, the circuitry may be configured to generate a pacing pulse, the timing of which may be based at least in part on the measure of volume of the ventricle at two or more of the plurality of times during the cardiac cycle.

Alternatively or additionally to any of the examples above, in another example, the LCP may further comprise a pressure sensor secured relative to the housing and is operationally coupled to the environment outside of the housing.

In another example, a method for detecting an atrial fiducial using a leadless cardiac pacemaker (LCP) that is implanted in a ventricle of a patient's heart, wherein the LCP has first electrode and a second electrode spaced from the first electrode may comprise identifying a measure of impedance between the first electrode and the second electrode of the LCP at each of a plurality of times during a cardiac cycle of the patient's heart, wherein each measure of impedance represents a measure of volume of the ventricle in which the LCP is implanted and determining the atrial fiducial based at least in part on the measure of volume of the ventricle at two or more of the plurality of times during the cardiac cycle.

Alternatively or additionally to any of the examples above, in another example, the method may further comprise generating a pacing pulse, the timing of which is based at least in part on the determined atrial fiducial.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 10C is a plan view of the example leadless cardiac pacing device of FIG. 8 implanted within a heart in a third configuration.

Figure 1:
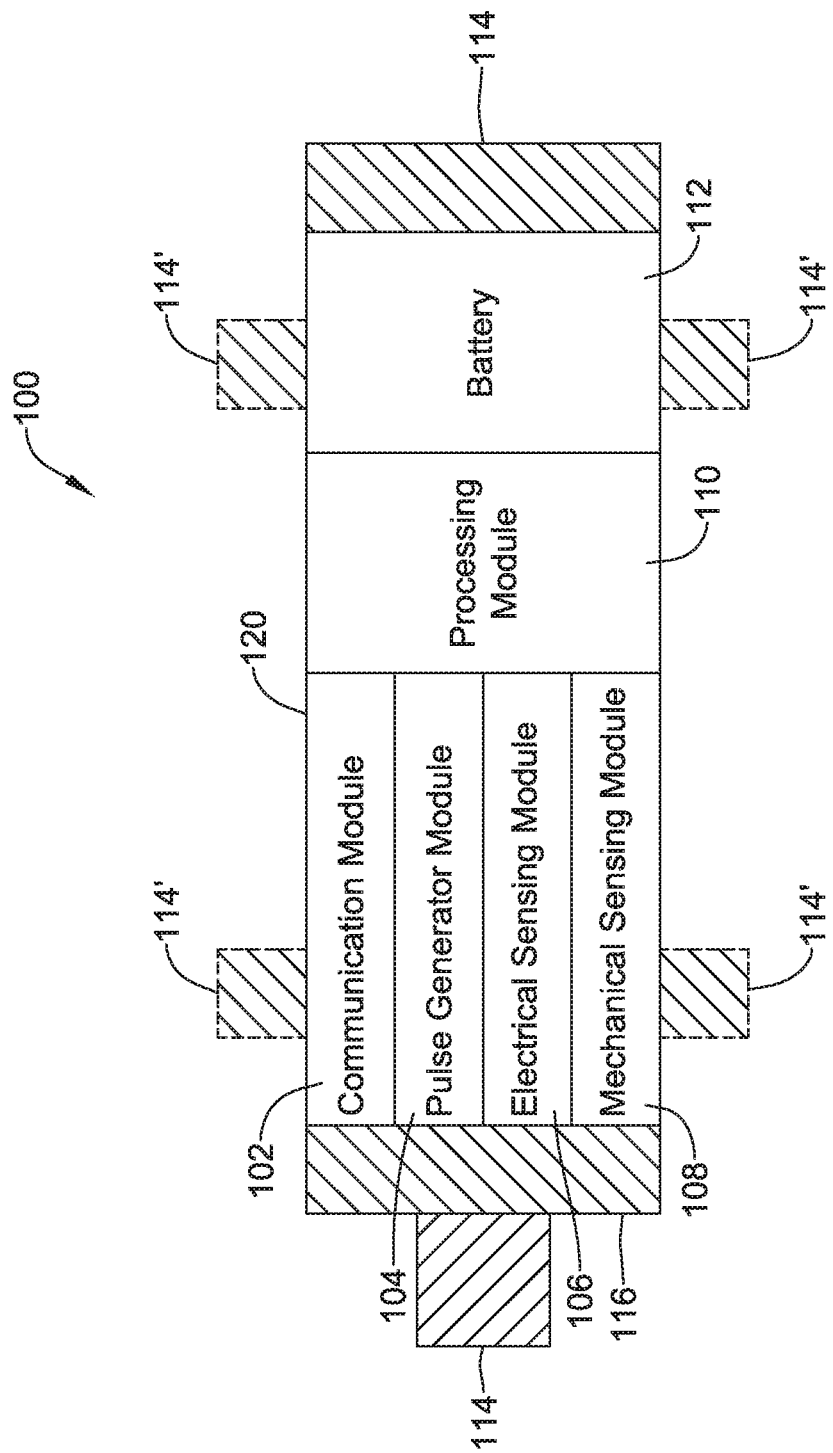
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may initiate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely desynchronized and the heart pumps very little to no blood. Implantable medical devices, which may be configured to determine occurrences of such cardiac abnormalities or arrhythmias and deliver one or more types of electrical stimulation therapy to patient's hearts, may help to terminate or alleviate these and other cardiac conditions.

FIG. 1 depicts an illustrative leadless cardiac pacemaker (LCP) that may be implanted into a patient and may operate to prevent, control, or terminate cardiac arrhythmias in patients by, for example, appropriately employing one or more therapies (e.g. anti-tachycardia pacing (ATP) therapy, Cardiac Resynchronization Therapy (CRT), bradycardia therapy, defibrillation pulses, or the like). As can be seen in FIG. 1, the LCP 100 may be a compact device with all components housed within the LCP 100 or directly on the housing 120. In the example shown in FIG. 1, the LCP 100 may include a communication module 102, a pulse generator module 104, an electrical sensing module 106, a mechanical sensing module 108, a processing module 110, a battery 112, and electrodes 114. The LCP 100 may include more or less modules, depending on the application.

The communication module 102 may be configured to communicate with devices such as sensors, other medical devices, and/or the like, that are located externally to the LCP 100. Such devices may be located either external or internal to the patient's body. Irrespective of the location, remote devices (i.e. external to the LCP 100 but not necessarily external to the patient's body) can communicate with the LCP 100 via the communication module 102 to accomplish one or more desired functions. For example, the LCP 100 may communicate information, such as sensed electrical signals, data, instructions, messages, etc., to an external medical device through the communication module 102. The external medical device may use the communicated signals, data, instructions and/or messages to perform various functions, such as determining occurrences of arrhythmias, delivering electrical stimulation therapy, storing received data, analyzing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, analyzing received data, and/or performing any other suitable function. The communication module 102 may be configured to use one or more methods for communicating with remote devices. For example, the communication module 102 may communicate via radiofrequency (RF) signals, inductive coupling, optical signals, acoustic signals, conducted communication signals, and/or any other signals suitable for communication.

In the example shown in FIG. 1, the pulse generator module 104 may be electrically connected to the electrodes 114. In some examples, LCP 100 may include one or more additional electrodes 114'. In such examples, the pulse generator 104 may also be electrically connected to the additional electrodes 114'. The pulse generator module 104 may be configured to generate electrical stimulation signals. For example, the pulse generator module 104 may generate electrical stimulation signals by using energy stored in a battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, Cardiac Resynchronization Therapy (CRT), and cardioversion/defibrillation therapy.

In some examples, the LCP 100 may not include a pulse generator 104 or may turn off the pulse generator 104. When so provided, the LCP 100 may be a diagnostic only device. In such examples, the LCP 100 may not deliver electrical stimulation therapy to a patient. Rather, the LCP 100 may collect data about cardiac electrical activity and/or physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart, cardiac electrical signals sensed by the LCP 100 through the electrodes 114/114' may represent ventricular cardiac electrical signals. The mechanical sensing module 108 may include one or more sensors, such as an accelerometer, a blood pressure sensor, a heart sound sensor, a blood-oxygen sensor, a temperature sensor, a flow sensor and/or any other suitable sensors that are configured to measure one or more mechanical and/or chemical parameters of the patient. Both the electrical sensing module 106 and the mechanical sensing module 108 may be connected to a processing module 110, which may provide signals representative of the sensed mechanical parameters. Although described with respect to FIG. 1 as separate sensing modules, in some cases, the electrical sensing module 106 and the mechanical sensing module 108 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to LCP 100 may have an insulative portion that electrically isolates the electrodes 114/114' from adjacent electrodes, the housing 120, and/or other parts of the LCP 100.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, occurrences and, in some cases, types of arrhythmias. Based on any determined arrhythmias, the processing module 110 may control the pulse generator module 104 to generate electrical stimulation in accordance with one or more therapies to treat the determined arrhythmia(s). The processing module 110 may further receive information from the communication module 102. In some examples, the processing module 110 may use such received information to help determine whether an arrhythmia is occurring, determine a type of arrhythmia, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 112 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
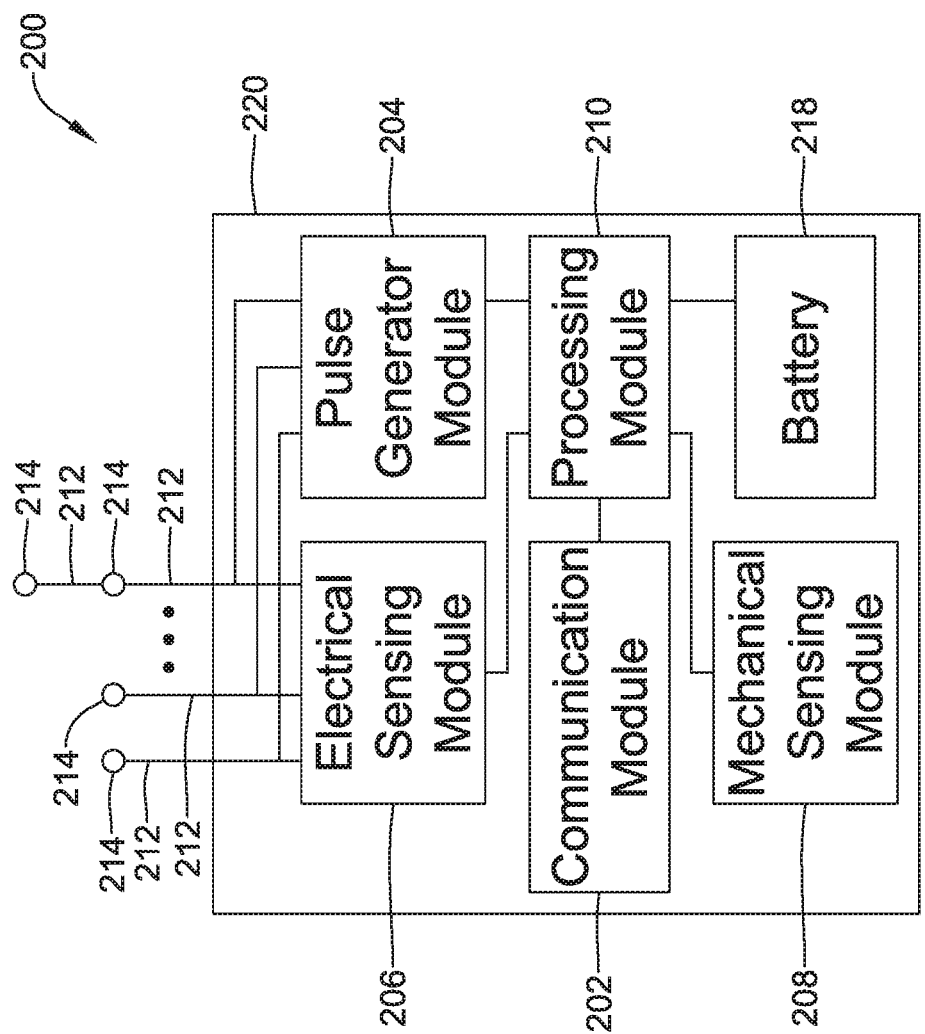
FIG. 2 is a schematic block diagram of another medical device (MD), which may be used in conjunction with an LCP 100 (FIG. 1) in order to detect and/or treat cardiac arrhythmias and other heart conditions.

FIG. 2 depicts an example of another medical device (MD) 200, which may be used in conjunction with an LCP 100 (FIG. 1) in order to detect and/or treat cardiac arrhythmias and other heart conditions. In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of the LCP 100. Additionally, the battery 218 may be similar to the battery 112 of the LCP 100. In some examples, the MD 200 may have a larger volume within the housing 220 than LCP 100. In such examples, the MD 200 may include a larger battery and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some of the leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously but adjacent the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In some instances, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some cases, the S-ICD lead may extend subcutaneously from the S-ICD can, around the sternum and may terminate adjacent the interior surface of the sternum.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy.

Figure 3:
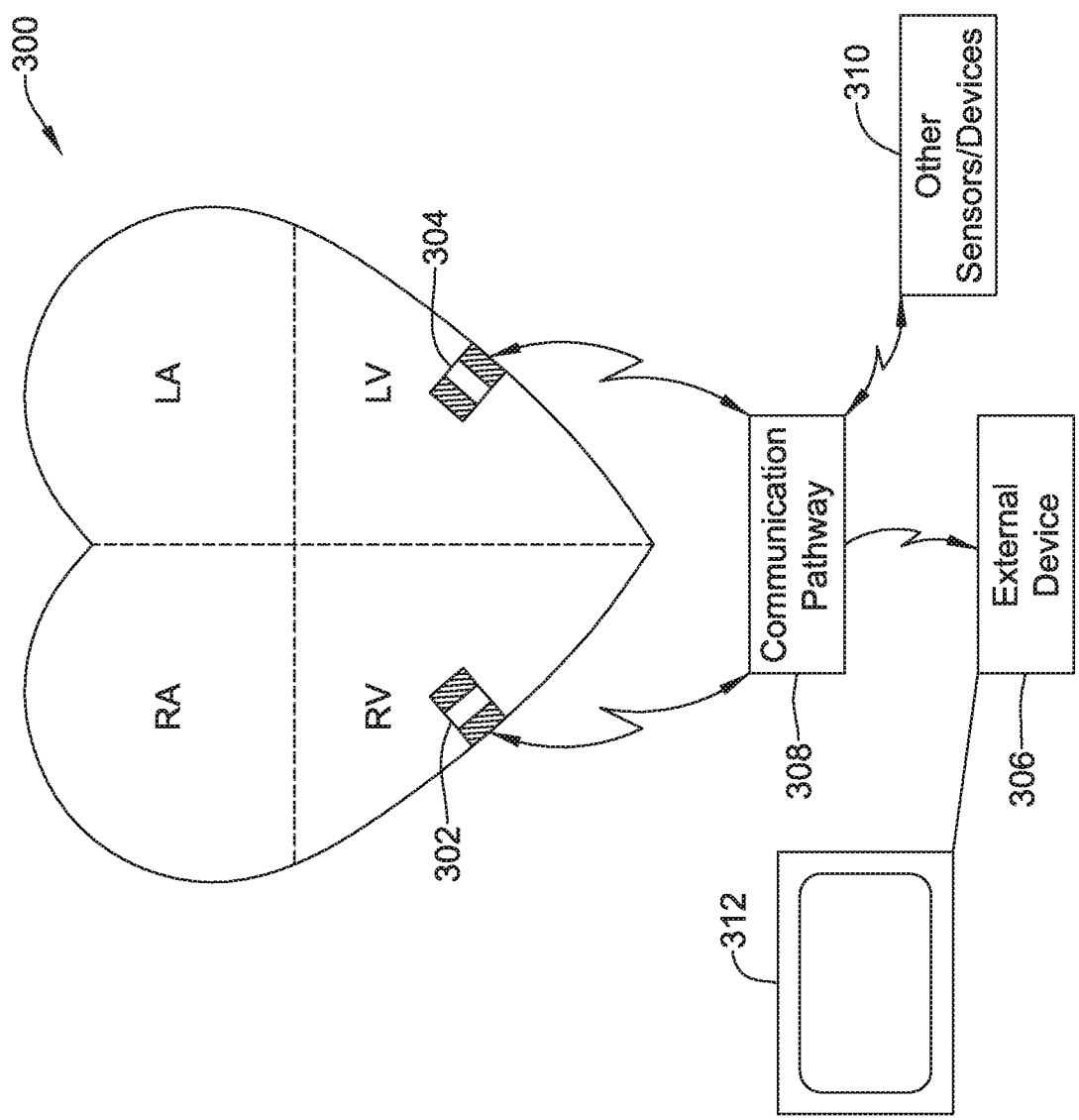
FIG. 3 is a schematic diagram of an exemplary medical system that includes multiple LCPs and/or other devices in communication with one another.

FIG. 3 shows an example medical device system with a communication pathway through which multiple medical devices 302, 304, 306, and/or 310 may communicate. In the example shown, the medical device system 300 may include LCPs 302 and 304, an external medical device 306, and other sensors/devices 310. The external device 306 may be any of the devices described previously with respect to MD 200. In some embodiments, the external device 306 may be provided with or be in communication with a display 312. The display 312 may be a personal computer, tablet computer, smart phone, laptop computer, or other display as desired. In some instances, the display 312 may include input means for receiving an input from a user. For example, the display 312 may also include a keyboard, mouse, actuatable buttons, or a touchscreen display. These are just examples. The other sensors/devices 310 may be any of the devices described previously with respect to the MD 200. In some instances, the other sensors/devices 310 may include a sensor, such as an accelerometer or blood pressure sensor, or the like. In some cases, the other sensors/devices 310 may include an external programmer device that may be used to program one or more devices of the system 300.

Various devices of the system 300 may communicate via a communication pathway 308. For example, the LCPs 302 and/or 304 may sense intrinsic cardiac electrical signals and may communicate such signals to one or more other devices 302/304, 306, and 310 of the system 300 via the communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. In another example, the LCPs 302 and/or 304 may sense indications of blood pressure (e.g. via one or more pressure sensors) and indications of volume (e.g. via an impedance between the electrodes of an LCP or between LCPs). In one example, one or more of the devices 302/304 may receive such signals and, based on the received signals, determine a pressure-volume loop, and in some cases may communicate such information to one or more other devices 302/304, 306, and 310 of the system 300 via the communication pathway 308.

It is contemplated that the communication pathway 308 may communicate using RF signals, inductive coupling, optical signals, acoustic signals, or any other signals suitable for communication. Additionally, in at least some examples, the device communication pathway 308 may comprise multiple signal types. For instance, the other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through the other sensors/devices 310, where the LCPs 302/304 send signals to the other sensors/devices 310, and the other sensors/devices 310 relay the received signals to the external device 306.

In some cases, the communication pathway 308 may include conducted communication. Accordingly, devices of the system 300 may have components that allow for such conducted communication. For instance, the devices of the system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 4:
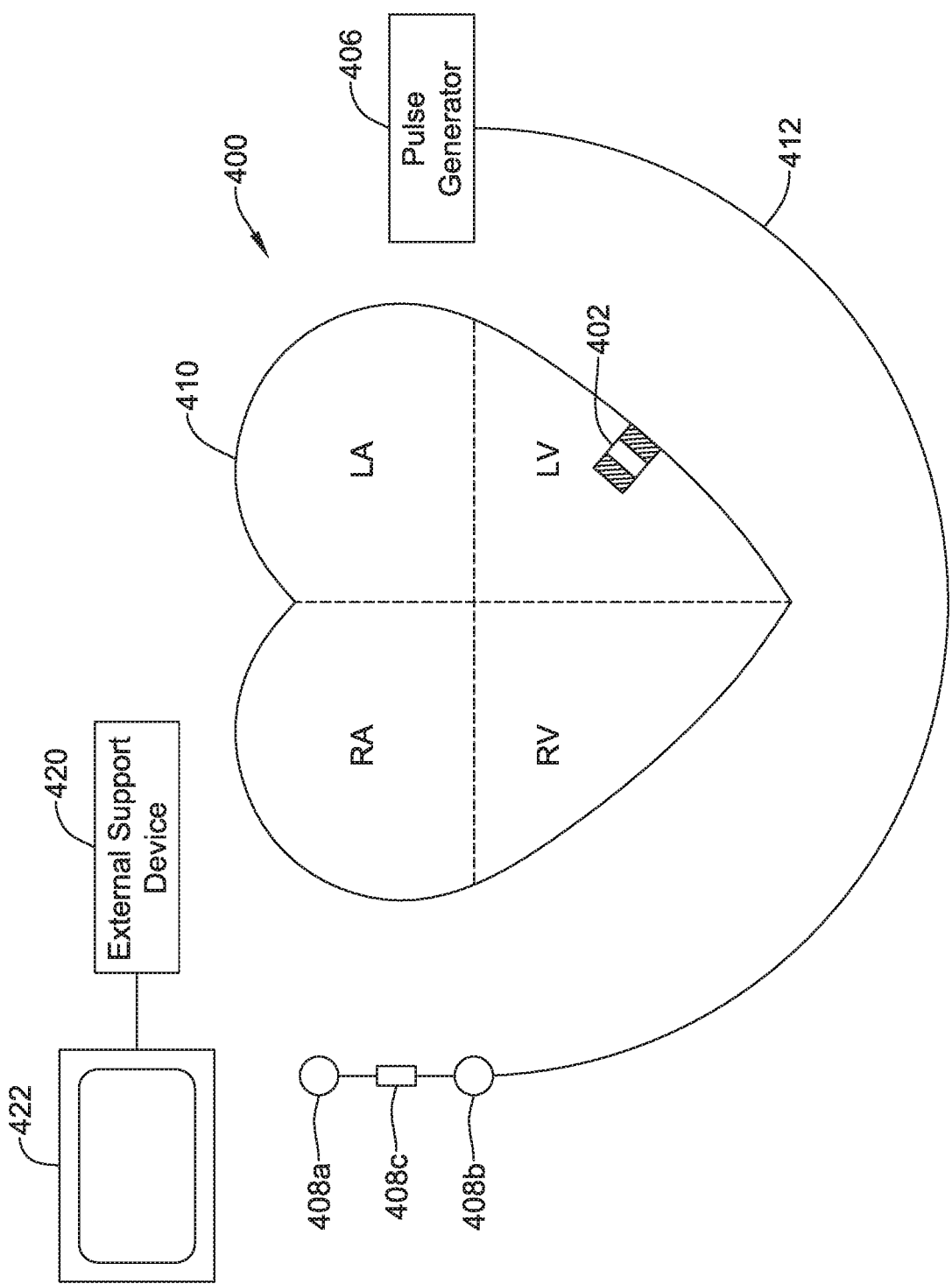
FIG. 4 is a schematic diagram of an exemplary medical system that includes an LCP and another medical device, in accordance with yet another example of the present disclosure.
Figure 5:
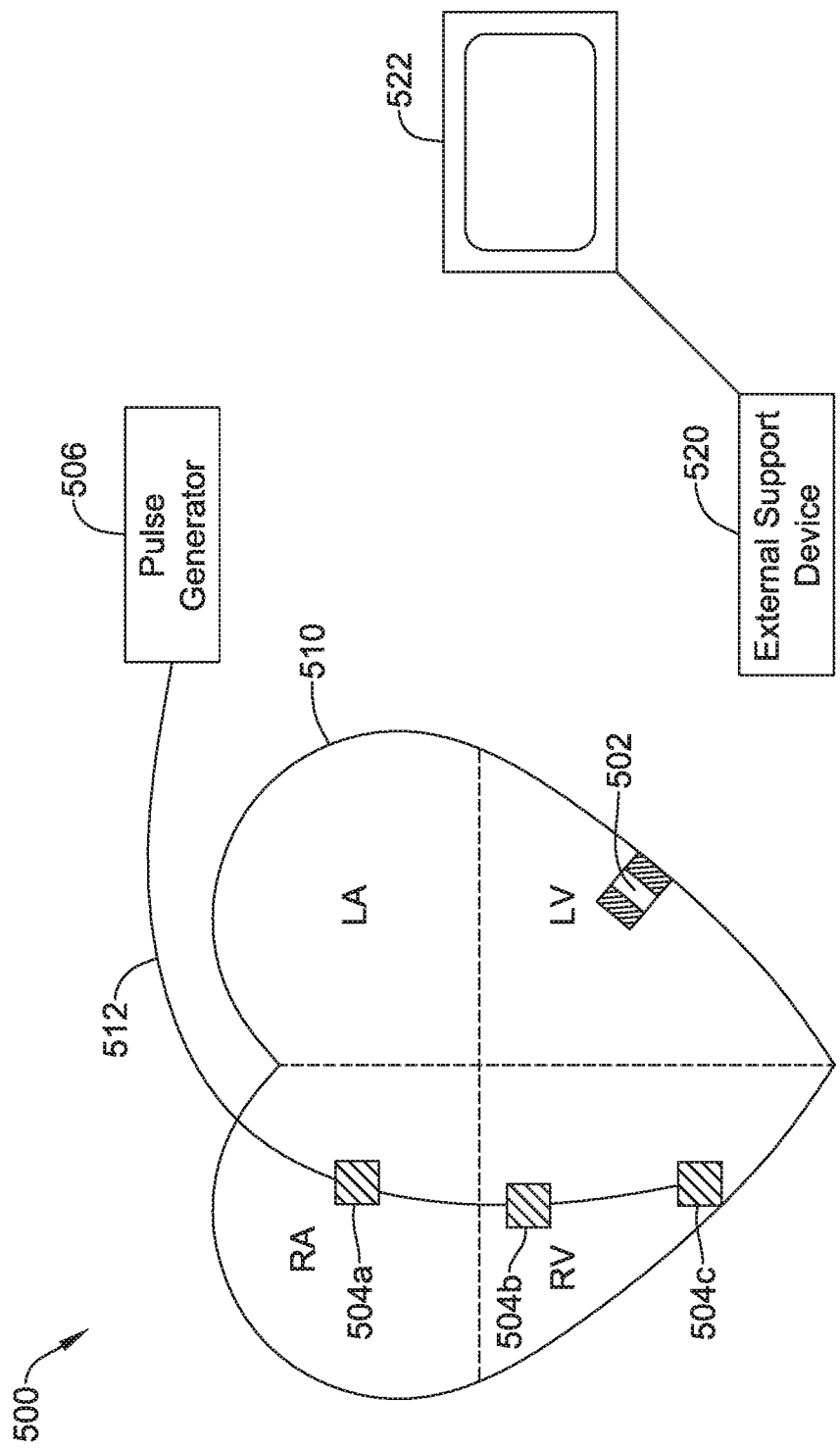
FIG. 5 is a schematic diagram of an exemplary medical system that includes an LCP and another medical device, in accordance with yet another example of the present disclosure.

FIGS. 4 and 5 show illustrative medical device systems that may be configured to operate according to techniques disclosed herein. In FIG. 4, an LCP 402 is shown fixed to the interior of the left ventricle of the heart 410, and a pulse generator 406 is shown coupled to a lead 412 having one or more electrodes 408a, 408b, 408c. In some cases, the pulse generator 406 may be part of a subcutaneous implantable cardioverter-defibrillator (S-ICD), and the one or more electrodes 408a, 408b, 408c may be positioned subcutaneously adjacent the heart. In some cases, the S-ICD lead may extend subcutaneously from the S-ICD can, around the sternum and one or more electrodes 408a, 408b, 408c may be positioned adjacent the interior surface of the sternum. In some cases, the LCP 402 may communicate with the subcutaneous implantable cardioverter-defibrillator (S-ICD).

In some cases, the LCP 302 may be in the right ventricle, right atrium or left atrium of the heart, as desired. In some cases, more than one LCP 302 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

In FIG. 5, an LCP 502 is shown fixed to the interior of the left ventricle of the heart 510, and a pulse generator 506 is shown coupled to a lead 512 having one or more electrodes 504a, 504b, 504c. In some cases, the pulse generator 506 may be part of an implantable cardiac pacemaker (ICP) and/or an implantable cardioverter-defibrillator (ICD), and the one or more electrodes 504a, 504b, 504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. The external support devices 420 and 520 can be used to perform functions such as device identification, device programming and/or transfer of real-time and/or stored data between devices using one or more of the communication techniques described herein. As one example, communication between the external support device 420 and the pulse generator 406 is performed via a wireless mode, and communication between the pulse generator 406 and the LCP 402 is performed via a conducted mode. In some examples, communication between the LCP 402 and the external support device 420 is accomplished by sending communication information through the pulse generator 406. However, in other examples, communication between the LCP 402 and the external support device 420 may be via a communication module. In some embodiments, the external support devices 420, 520 may be provided with or be in communication with a display 422, 522. The display 422, 522 may be a personal computer, tablet computer, smart phone, laptop computer, or other display as desired. In some instances, the display 422, 522 may include input means for receiving an input from a user. For example, the display 422, 522 may also include a keyboard, mouse, actuatable buttons, or be a touchscreen display. These are just examples.

FIGS. 4-5 illustrate two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as the pulse generator 406 or 506, with at least one LCP capable of delivering defibrillation therapy. In yet other examples, the configuration or placement of the medical devices, leads, and/or electrodes may be different from those depicted in FIGS. 4 and 5. Accordingly, it should be recognized that numerous other medical device systems, different from those depicted in FIGS. 4 and 5, may be operated in accordance with techniques disclosed herein. As such, the examples shown in FIGS. 4 and 5 should not be viewed as limiting in any way.

Figure 6:
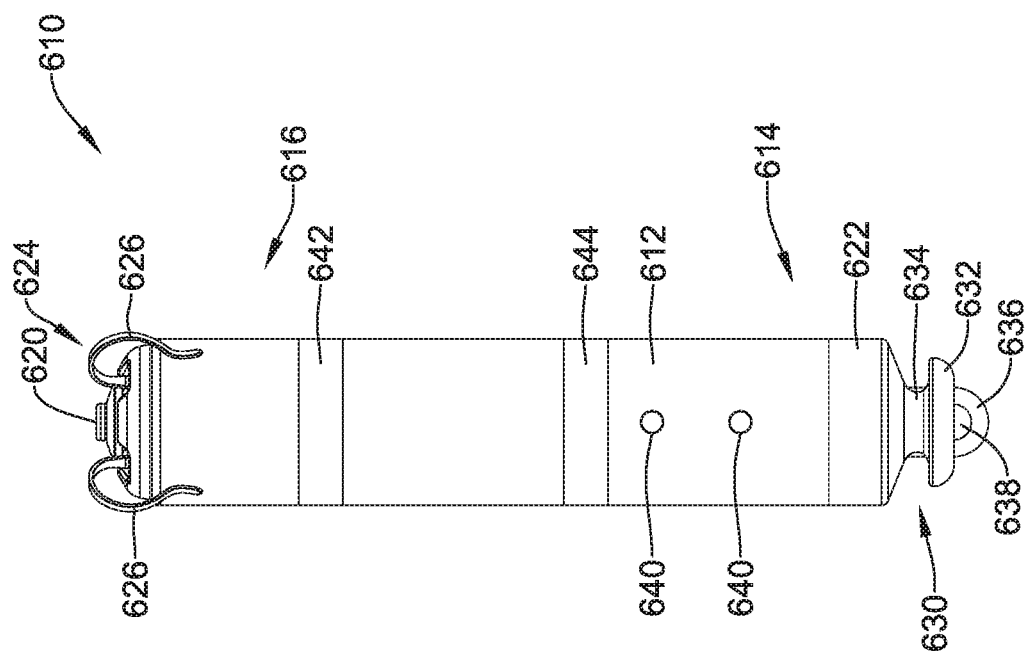
FIG. 6 is a side view of an illustrative implantable leadless cardiac pacing device.

FIG. 6 is a side view of an illustrative implantable leadless cardiac pacemaker (LCP) 610. The LCP 610 may be similar in form and function to the LCP 100 described above. The LCP 610 may include any of the modules and/or structural features described above with respect to the LCP 100 described above. The LCP 610 may include a shell or housing 612 having a proximal end 614 and a distal end 616. The illustrative LCP 610 includes a first electrode 620 (e.g. cathode) secured relative to the housing 612 and positioned adjacent to the distal end 616 of the housing 612, and a second electrode 622 (e.g. anode) secured relative to the housing 612 and positioned adjacent to the proximal end 614 of the housing 612. In some cases, the housing 612 may include a conductive material and may be insulated along a portion of its length. A section along the proximal end 614 may be free of insulation so as to define the second electrode 622. In some instances, the LCP 610 may include two or more additional electrodes 642, 644 positioned between the first electrode 620 and the second electrode 622. However, it is not required that the electrodes 642, 644 be positioned between the first electrode 620 and the second electrode 622. For example, the electrodes 642, 644 may be on a tail, as further detailed below.

It is contemplated that the electrodes 620, 622, 642, 644 may be sensing and/or pacing electrodes to provide electrotherapy and/or sensing capabilities. In one example, the first electrode 620 may be capable of being positioned against or may otherwise contact the cardiac tissue of the heart while the second, third, and fourth electrodes 622, 642, 644 may be spaced away from the first electrode 620. The first, second, third and/or fourth electrodes 620, 622, 642, 644 may be exposed to the environment outside the housing 612 (e.g. to blood and/or tissue).

In some cases, the LCP 610 may include a pulse generator (e.g., electrical circuitry) and a power source (e.g., a battery) within the housing 612 to provide electrical signals to the electrodes 620, 622, 642, 644 to control the pacing/sensing electrodes 620, 622, 642, 644. While not explicitly shown, the LCP 610 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 612. Electrical communication between the pulse generator and the electrodes 620, 622, 642, 644 may provide electrical stimulation to heart tissue and/or sense a physiological condition.

Figure 7A:
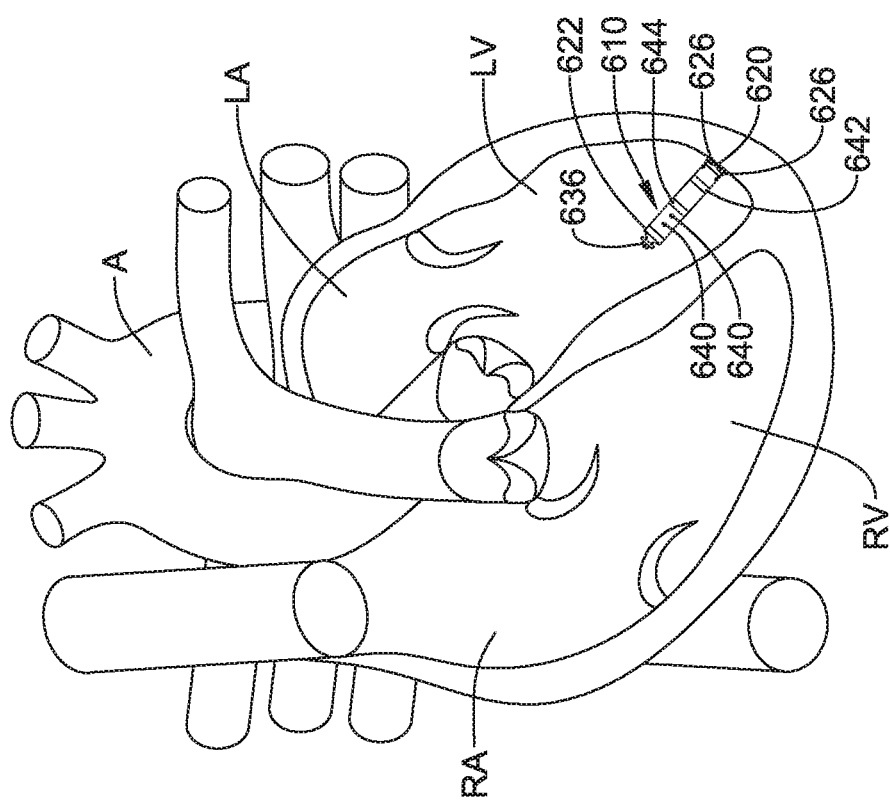
FIG. 7A is a plan view of an example leadless cardiac pacing device implanted within a heart during ventricular filling.
Figure 7B:
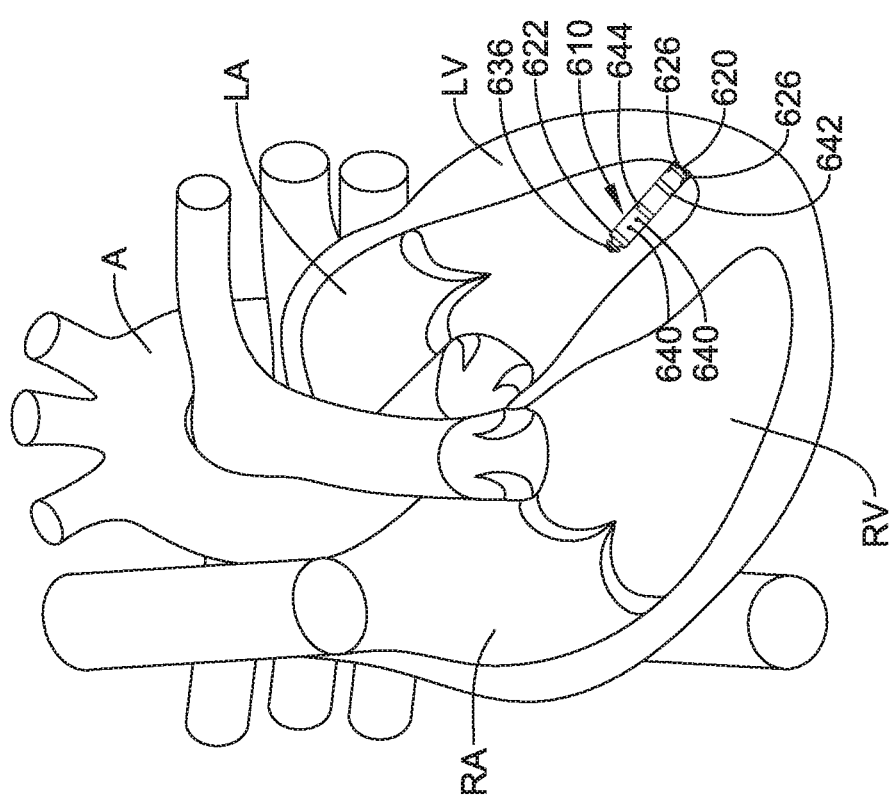
FIG. 7B is a plan view of an example leadless cardiac pacing device implanted within a heart during ventricular contraction.

In the example shown, the LCP 610 includes a fixation mechanism 624 proximate the distal end 616 of the housing 612. The fixation mechanism 624 is configured to attach the LCP 610 to a wall of the heart H, or otherwise anchor the LCP 610 to the anatomy of the patient. As shown in FIGS. 6, 7A, and 7B, in some instances, the fixation mechanism 624 may include one or more, or a plurality of hooks or tines 626 anchored into the cardiac tissue of the heart H to attach the LCP 610 to a tissue wall. In other instances, the fixation mechanism 624 may include one or more, or a plurality of passive tines, configured to entangle with trabeculae within the chamber of the heart H and/or a helical fixation anchor configured to be screwed into a tissue wall to anchor the LCP 610 to the heart H. These are just examples.

The LCP 610 may further include a docking member 630 proximate the proximal end 614 of the housing 612. The docking member 630 may be configured to facilitate delivery and/or retrieval of the LCP 610. For example, the docking member 630 may extend from the proximal end 614 of the housing 612 along a longitudinal axis of the housing 612. The docking member 630 may include a head portion 632 and a neck portion 634 extending between the housing 612 and the head portion 632. The head portion 632 may be an enlarged portion relative to the neck portion 634. For example, the head portion 632 may have a radial dimension from the longitudinal axis of the LCP 610 that is greater than a radial dimension of the neck portion 634 from the longitudinal axis of the LCP 610. In some cases, the docking member 630 may further include a tether retention structure 636 extending from or recessed within the head portion 632. The tether retention structure 636 may define an opening 638 configured to receive a tether or other anchoring mechanism therethrough. While the retention structure 636 is shown as having a generally "U-shaped" configuration, the retention structure 636 may take any shape that provides an enclosed perimeter surrounding the opening 638 such that a tether may be securably and releasably passed (e.g. looped) through the opening 638. In some cases, the retention structure 636 may extend though the head portion 632, along the neck portion 634, and to or into the proximal end 614 of the housing 612. The docking member 630 may be configured to facilitate delivery of the LCP 610 to the intracardiac site and/or retrieval of the LCP 610 from the intracardiac site. While this describes one example docking member 630, it is contemplated that the docking member 630, when provided, can have any suitable configuration.

It is contemplated that the LCP 610 may include one or more pressure sensors 640 coupled to or formed within the housing 612 such that the pressure sensor(s) is exposed to and/or operationally coupled to the pressure in the environment outside the housing 612. In some cases, the pressure sensor 640 may be coupled to an exterior surface of the housing 612. In other cases, the pressures sensor 640 may be positioned within the housing 612 with a pressure acting on the housing and/or a port on the housing 612 to affect the pressure sensor 640. The one or more pressure sensors 640 may be used to measure blood pressure within the heart. For example, if the LCP 610 is placed in the left ventricle, the pressure sensor(s) 640 may measure the pressure within the left ventricle. If the LCP 610 is placed in another portion of the heart (such as one of the atriums or the right ventricle), the pressures sensor(s) may measure the pressure within that portion of the heart. The pressure sensor(s) 640 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 640 may be part of a mechanical sensing module described herein. It is contemplated that the pressure measurements obtained from the pressures sensor(s) 640 may be used to generate a pressure curve over one or more cardiac cycles. In some cases, the pressure readings may be taken in combination with impedance measurements (e.g. the impedance between, for example, electrodes 620 and 622) to generate a pressure-impedance loop for one or more cardiac cycles. The impedance may be a surrogate for chamber volume, and thus the pressure-impedance loop may be representative of a pressure-volume loop for the heart H. In some instances, the impedance may be used to identify volume changes within a chamber of the heart.

In some embodiments, the LCP 610 may be configured to identify a measure of impedance between pairs of the electrodes 620, 622, 642, 644 at a plurality of times during a cardiac cycle. More generally, the impedance may be measured between any suitable electrode pair, and may include any of additional electrodes 114' described above. In some cases, the impedance may be measured between two spaced LCP's, such as two LCP's implanted within the same chamber (e.g. LV) of the heart H, or two LCP's implanted in different chambers of the heart H (e.g. RV and LV). The processing module of the LCP 610 and/or external support device(s) may derive a measure of cardiac volume (of the chamber in which the LCP 610 is implanted) from intracardiac impedance measurements made between pairs or groups of the electrodes 620, 622, 642, 644 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy, ultrasound, or the like, and the measured impedance may be correlated to the actual cardiac volume.

In some cases, the LCP 610 (e.g. the circuitry) may be configured to generate a pacing pulse, the time of which is based at least in part on the measure of volume of the ventricle (or other chamber) at two or more of the plurality of times during the cardiac cycle.

In some cases, the LCP 610 may include energy delivery circuitry operatively coupled to the first electrode 620, the second electrode 622, the third electrode 642, and/or the fourth electrode 644 for causing a current to flow between pairs of electrodes in order to determine the impedance between two electrodes. In some cases, it is desirable to provide the current between a pair of driving electrodes and to sense a resulting voltage between a pair of sensing electrodes to determine the impedance between the sensing electrodes, wherein the sensing electrodes are physically and logically different electrodes from the driving electrodes. The LCP 610 may include detection circuitry operatively coupled to the sensing electrodes when current is provided between the driving electrodes. When the energy delivery circuitry delivers a current between the driving electrodes, the detection circuitry may measure a resulting voltage between the sensing electrodes to determine the impedance between the sensing electrodes. It is contemplated that the energy delivery circuitry may also be configured to deliver pacing pulses via the first electrode 620 and one of the second electrode 622, the third electrode 642, or the fourth electrode 644. In some cases, the LCP 610 and/or other external device may include circuitry configured to analyze the impedance measurements between the selected electrodes and select a combination of delivery electrodes and sensing electrodes that provide the best results.

In some embodiments, the impedance may be measured between electrodes on different devices and/or in different heart chambers. For example, impedance may be measured between a first electrode in the left ventricle and a second electrode in the right ventricle. In another example, impedance may be measured between a first electrode of a first LCP in the left ventricle and a second LCP in the left ventricle. In yet another example, impedance may be measured from a current injected from outside of the heart. For example, a medical device (such as, but not limited to an S-ICD), may inject a known current into the heart and the LCP implanted in the heart H may measure a voltage resulting from the injected current to determine the impedance. These are just some examples.

The use of multiple electrode vectors and/or the availability of multiple electrode vectors may allow for vector selection to select a volume of interest. Since impedance is only a surrogate for volume, measuring an impedance along a vector that encompasses more of the heart chamber of interest may produce a more accurate result. In some cases, alignment of a selected vector may changes due to movement of the LCP, posture of the patient, and other factors. In some cases, the vector may be changed based on one or more factors.

FIG. 7A is a plan view of the example leadless cardiac pacing device 610 implanted within a left ventricle LV of the heart H during ventricular filling. The right ventricle RV, right atrium RA, left atrium LA, and aorta A are also illustrated. FIG. 7B is a plan view of the leadless cardiac pacing device 610 implanted within a left ventricle of the heart H during ventricular contraction. These figures illustrate how the volume of the left ventricle may change over a cardiac cycle. As can be seen in FIGS. 7A and 7B, the volume of the left ventricle during ventricular filling is larger than the volume of the left ventricle of the heart during ventricular contraction.

In some cases, the processing module and/or other control circuitry of the LCP 610 may capture, at a time point within each of one or more cardiac cycles, an impedance between at least one pair of electrodes. The impedance may be used as a surrogate for blood volume in the heart. Monitoring a derivative (e.g. slope) of the volume (e.g. dV/dt) over a cardiac cycle may allow for the determination of the volume of blood entering the left ventricle that is associated with passive filling, and a volume of blood entering the left ventricle that is associated with an atrial contraction (e.g. atrial kick). The change in rate of volume filling, and timing of such change in rate of volume filling, may help identify an atrial fiducial associated with an atrium contraction. The atrial fiducial may then be used to time a pacing pulse for the ventricle in support of cardiac resynchronization therapy (CRT). For example, the timing of the ventricle pacing pulse may be adjusted to maximize the amount of blood entering the left ventricle through passive filling. In another example, the timing of the ventricle pacing pulse may be adjusted to maximize the dP/dt (slope of pressure versus time). These are just some examples. In some instances, this may include adjusting the AV delay relative to the atrial fiducial. In some cases, the measured impedance, and corresponding chamber volume, may be used to support management of a non-CRT cardiac therapy, patient health status monitoring and/or any other suitable goal.

Figure 8:
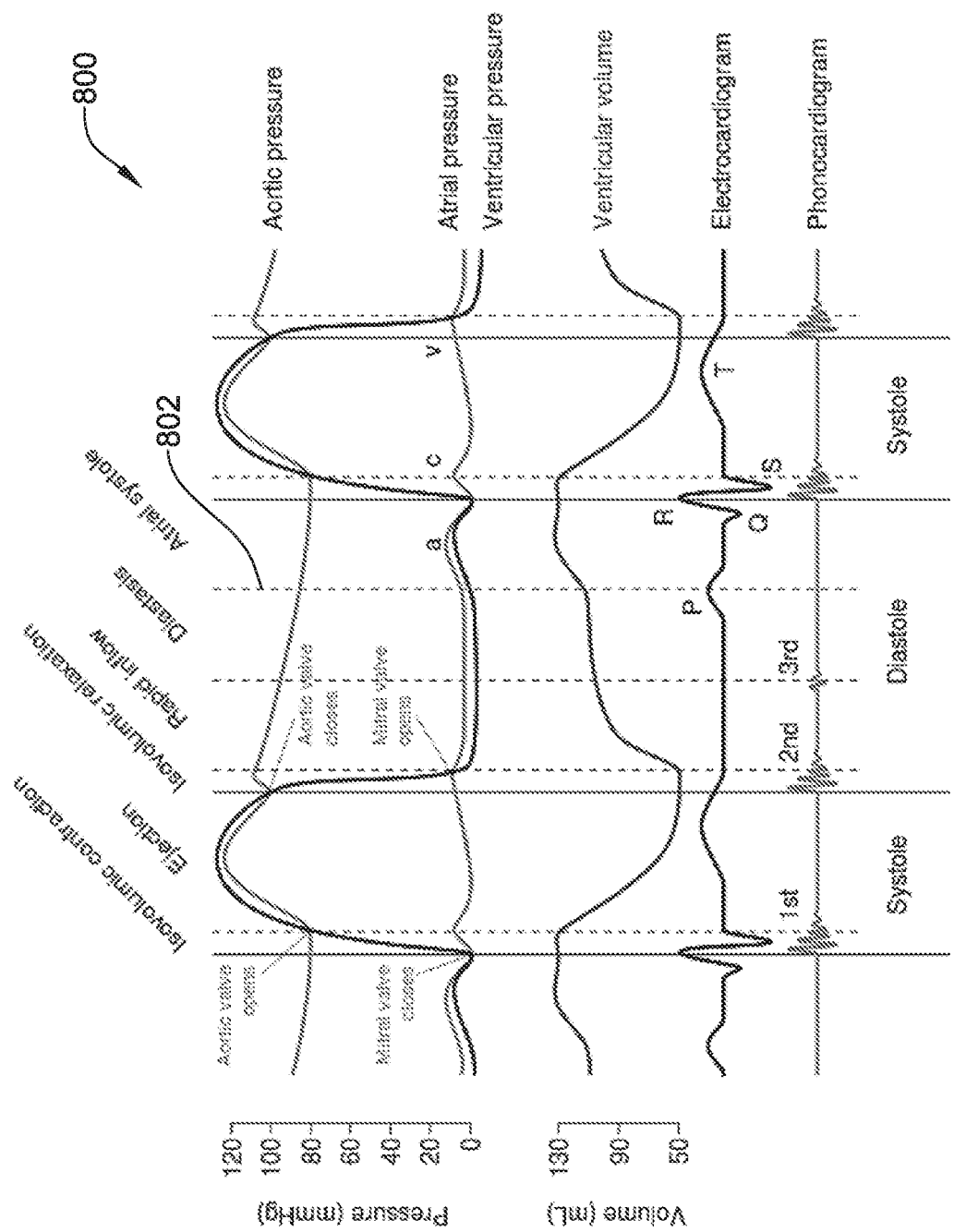
FIG. 8 is a graph showing example pressures and volumes within the heart over time.

FIG. 8 is a graph 800 showing example pressures and volumes within a heart over time. More specifically, FIG. 8 depicts the aortic pressure, left ventricular pressure, left atrial pressure, left ventricular volume, an electrocardiogram (ECG or egram), and heart sounds of the heart H. A cardiac cycle may begin with diastole, and the mitral valve opens. The ventricular pressure falls below the atrial pressure, resulting in the ventricular filling with blood. During ventricular filling, the aortic pressure slowly decreases as shown. The atrial contraction may occur at a time indicated at line 802. As can be seen, the change in volume of the left ventricle with respect to time changes significantly at this point. As discussed above, this derivative may be used to identify the atrial kick.

During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricle volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats. Cardiac pressure curves for the pulmonary artery, the right atrium, and the right ventricle, and the cardiac volume curve for the right ventricle, similar to those illustrated in FIG. 8 for the left part of the heart, may be likewise generated. Typically, the cardiac pressure in the right ventricle is lower than the cardiac pressure in the left ventricle.

In one example, the heart sound signals can be recorded using acoustic sensors, (for example, a microphone), which capture the acoustic waves resulted from heart sounds. In another example, the heart sound signals can be recorded using accelerometers or pressure sensors that capture the accelerations or pressure waves caused by heart sounds. The heart sound signals can be recorded within or outside the heart. These are just examples.

Figure 9:
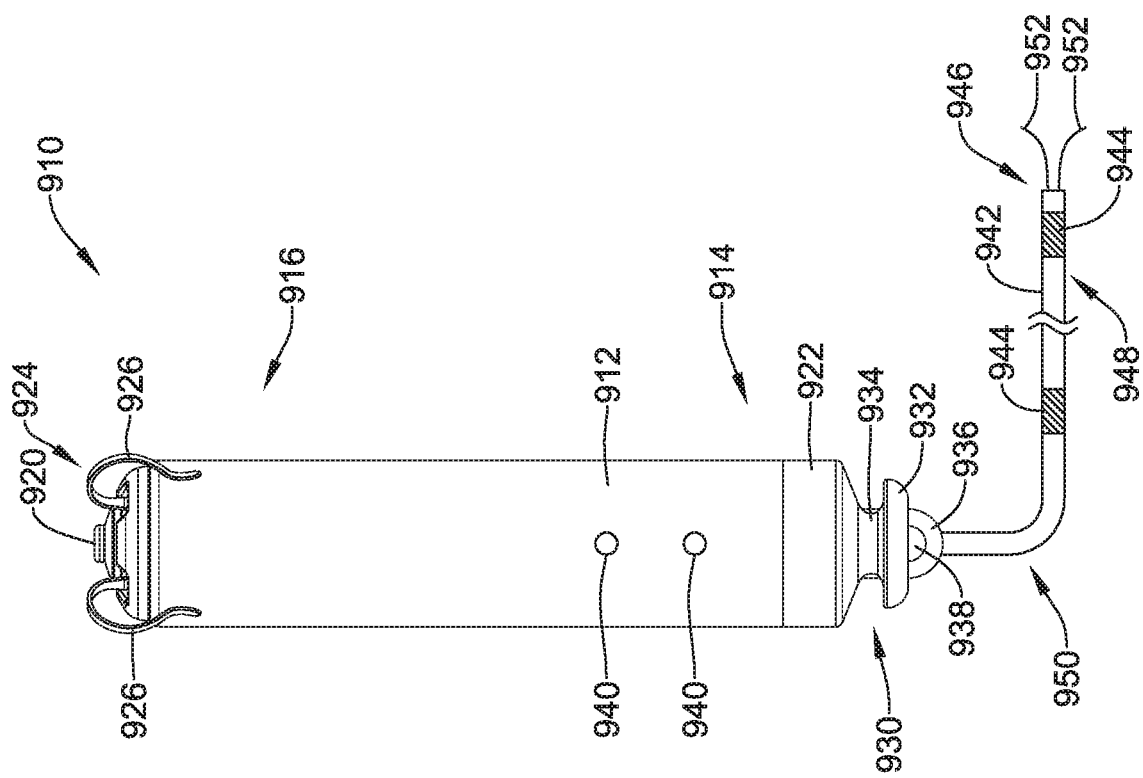
FIG. 9 is a side view of another illustrative implantable leadless cardiac pacing device.

FIG. 9 is a side view of another illustrative implantable leadless cardiac pacemaker (LCP) 910. The LCP 910 may be similar in form and function to the LCP 100 described above. The LCP 910 may include any of the modules and/or structural features described above with respect to the LCP 100 described above. The LCP 910 may include a housing having a rigid shell or body 912 and a flexible extension element or tail 942. The rigid body 912 includes a proximal end 914 and a distal end 916. The tail 942 is shown extending from the proximal end 914 of the rigid body 912, as will be described in more detail below. The illustrative LCP 910 further includes a first electrode 920 secured relative to the rigid body 912 and positioned adjacent to the distal end 916 of the rigid body 912, and a second electrode 922 secured relative to the rigid body 912 and positioned adjacent to the proximal end 914 of the rigid body 912. While not explicitly shown, the LCP 910 may include one or more additional electrodes on the rigid body 912. However, this is not required. In some cases, the rigid body 912 may include a conductive material and may be insulated along a portion of its length. A section along the proximal end 914 may be free of insulation so as to define the second electrode 922. One or more electrode(s) 944 may be positioned adjacent to a proximal end 948 of the tail 942, as shown. The electrodes 920, 922, 944 may be sensing and/or pacing electrodes to provide electro-therapy and/or sensing capabilities. The first electrode 920 may be capable of being positioned against or may otherwise contact the cardiac tissue of the heart while the second and third (and/or additional) electrodes 922, 944 may be spaced away from the first electrode 920. The first, second, third, (and/or additional) electrodes 920, 922, 944 may be exposed to the environment outside the housing (e.g. to blood and/or tissue).

In some cases, the LCP 910 may include a pulse generator (e.g., electrical circuitry) and a power source (e.g., a battery) within the rigid body 912 to provide electrical signals to the electrodes 920, 922, 944 to control the pacing/sensing electrodes 920, 922, 944. While not explicitly shown, the LCP 910 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing. Electrical communication between the pulse generator and the electrodes 920, 922, 944 may provide electrical stimulation to heart tissue and/or sense a physiological condition.

In the example shown, the LCP 910 further includes a fixation mechanism 924 proximate the distal end 916 of the rigid body 912. The fixation mechanism 924 is configured to attach the LCP 910 to a wall of the heart H, or otherwise anchor the LCP 910 to the anatomy of the patient. As shown in FIGS. 9 and 10A-10C, in some instances, the fixation mechanism 924 may include one or more, or a plurality of hooks or tines 926 anchored into the cardiac tissue of the heart H to attach the LCP 910 to a tissue wall. In other instances, the fixation mechanism 924 may include one or more, or a plurality of passive tines, configured to entangle with trabeculae within the chamber of the heart H and/or a helical fixation anchor configured to be screwed into a tissue wall to anchor the LCP 910 to the heart H. These are just examples.

The tail 942 of the LCP 910 may include a fixation mechanism 946 proximate to the proximal end 948 of the tail 942. The fixation mechanism 946 is configured to attach the tail 942 to a wall of the heart H, or otherwise anchor the tail 942 to the anatomy of the patient. In some embodiments, the fixation mechanism 946 may be configured to fix the tail 942 at a location different from the first fixation mechanism 924. As shown in FIGS. 9 and 10A-10C, in some instances, the fixation mechanism 946 may include one or more, or a plurality of hooks or tines 952 anchored into the cardiac tissue of the heart H to attach the tail 942. In other instances, the fixation mechanism 946 may include one or more, or a plurality of passive tines, configured to entangle with trabeculae within the chamber of the heart H and/or a helical fixation anchor configured to be screwed into a tissue wall to anchor the tail 942 to the heart H. These are just examples. In some embodiments, the tail 942 may not include a fixation mechanism.

The LCP 910 may further include a docking member 930, shown proximate the proximal end 914 of the rigid body 912. The docking member 930 may be configured to facilitate delivery and/or retrieval of the LCP 910. For example, the docking member 930 may extend from the proximal end 914 of the rigid body 912 along a longitudinal axis of the rigid body 912. The docking member 930 may include a head portion 932 and a neck portion 934 extending between the rigid body 912 and the head portion 932. The head portion 932 may be an enlarged portion relative to the neck portion 934. For example, the head portion 932 may have a radial dimension from the longitudinal axis of the LCP 910 that is greater than a radial dimension of the neck portion 934 from the longitudinal axis of the LCP 910. In some cases, the docking member 930 may further include a tether retention structure 936 extending from or recessed within the head portion 932. The tether retention structure 936 may define an opening 938 configured to receive a tether or other anchoring mechanism therethrough. While the retention structure 936 is shown as having a generally "U-shaped" configuration, the retention structure 936 may take any shape that provides an enclosed perimeter surrounding the opening 938 such that a tether may be securably and releasably passed (e.g. looped) through the opening 938. In some cases, the retention structure 936 may extend though the head portion 932, along the neck portion 934, and to or into the proximal end 914 of the rigid body 912. The docking member 930 may be configured to facilitate delivery of the LCP 910 to the intracardiac site and/or retrieval of the LCP 910 from the intracardiac site. While this describes one example docking member 930, it is contemplated that the docking member 930, when provided, can have any suitable configuration.

The tail 942 may extend proximally from a distal end region 950 of the rigid body 912 and may be affixed to or adjacent the docking member 930. The tail 942 may extend proximally to a proximal end region 948. The tail 942 may include a conductive material and may be insulated along a portion of its length. A section along the proximal end region 948 may be free of insulation so as to define the third electrode 944. It is contemplated that the tail 942 may include two or more electrodes 944. When provided with multiple electrodes on the tail 942, the LCP 910 circuitry may be configured to select between the two or more electrodes to determine which, if any, is used in an impedance measurement. The tail 942 may be relatively flexible to allow it to be positioned at various locations with the heart, as illustrated in FIGS. 10-10C.

It is contemplated that the LCP 910 may include one or more pressure sensors 940 coupled to or formed within the housing such that the pressure sensor(s) is exposed to the pressure in the environment outside the housing. The pressure sensor(s) may be used to measure blood pressure within the heart. In one example, if the LCP 910 is placed in the left ventricle, the pressure sensor(s) 940 may measure the pressure within the left ventricle. If the LCP 910 is placed in another portion of the heart (such as one of the atriums or the right ventricle), the pressures sensor(s) may measure the pressure within that portion of the heart. The pressure sensor(s) 940 may include a MEMS device, such as a MEMS device with a pressure diaphragm and piezoresistors on the diaphragm, a piezoelectric sensor, a capacitor-Micromachined Ultrasonic Transducer (cMUT), a condenser, a micro-monometer, or any other suitable sensor adapted for measuring cardiac pressure. The pressures sensor(s) 940 may be part of a mechanical sensing module described herein. It is contemplated that the pressure measurements obtained from the pressures sensor(s) 940 may be used to generate a pressure curve over cardiac cycles. The pressure readings may be taken in combination with impedance measurements (e.g. the impedance between, for example, electrodes 920 and 922) to generate a pressure-impedance loop for one or more cardiac cycles. The impedance may be a surrogate for chamber volume, and thus the pressure-impedance loop may be representative of a pressure-volume loop for the heart H. In some instances, the impedance may be used to identify volume changes within a chamber of the heart In some embodiments, the LCP 910 may be configured to identify a measure of impedance between pairs of the electrodes 920, 922, 944 at a plurality of times during a cardiac cycle. More generally, the impedance may be measured between any suitable electrode pair, and may include any of additional electrodes 114' described above. In some cases, the impedance may be measured between two spaced LCP's, such as two LCP's implanted within the same chamber (e.g. LV) of the heart H, or two LCP's implanted in different chambers of the heart H (e.g. RV and LV). The processing module of the LCP 910 and/or external support device(s) may derive a measure of cardiac volume (of the chamber in which the LCP 910 is implanted) from intracardiac impedance measurements made between pairs or groups of the electrodes 920, 922, 944 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy, ultrasound, or the like, and the measured impedance may be correlated to the actual cardiac volume. In some cases, the LCP 910 (e.g. the circuitry) may be configured to generate a pacing pulse, the time of which is based at least in part on the measure of volume of the ventricle (or other chamber) at two or more of the plurality of times during the cardiac cycle.

In some cases, the LCP 910 may include energy delivery circuitry operatively coupled to electrodes 920, 922, 944 (or other electrodes) for causing a current to flow between pairs of electrodes in order to determine the impedance between two electrodes. In some cases, it is desirable to provide the current between a pair of driving electrodes and to sense a resulting voltage between a pair of sensing electrodes to determine the impedance between the sensing electrodes, wherein the sensing electrodes are physically and logically different electrodes from the driving electrodes. The LCP 910 may include detection circuitry operatively coupled to the sensing electrodes when current is provided between the driving electrodes. When the energy delivery circuitry delivers a current between the driving electrodes, the detection circuitry may measure a resulting voltage between the sensing electrodes to determine the impedance between the sensing electrodes. It is contemplated that the energy delivery circuitry may also be configured to deliver pacing pulses via the first electrode 920 and one of the other electrodes 922, 944 (or other electrodes). In some cases, the LCP 910 and/or other external device may include circuitry configured to analyze the impedance measurements between the selected electrodes and select a combination of delivery electrodes and sensing electrodes that provide the best results.

In some embodiments, the impedance may be measured between electrodes on different devices and/or in different heart chambers. For example, impedance may be measured between a first electrode in the left ventricle and a second electrode in the right ventricle. In another example, impedance may be measured between a first electrode of a first LCP in the left ventricle and a second LCP in the left ventricle. In yet another example, impedance may be measured from a current injected from outside of the heart. For example, a medical device (such as, but not limited to an S-ICD), may inject a known current into the heart and the LCP implanted in the heart H may measure a voltage resulting from the injected current to determine the impedance. These are just some examples.

The use of multiple electrode vectors and/or the availability of multiple electrode vectors may allow for vector selection to select a volume of interest. Since impedance is only a surrogate for volume, measuring an impedance along a vector that encompasses more of the heart chamber of interest may produce a more accurate result. In some cases, alignment of a selected vector may changes due to movement of the LCP, posture of the patient, and other factors. In some cases, the vector may be changed based on one or more factors.

Figure 10A:
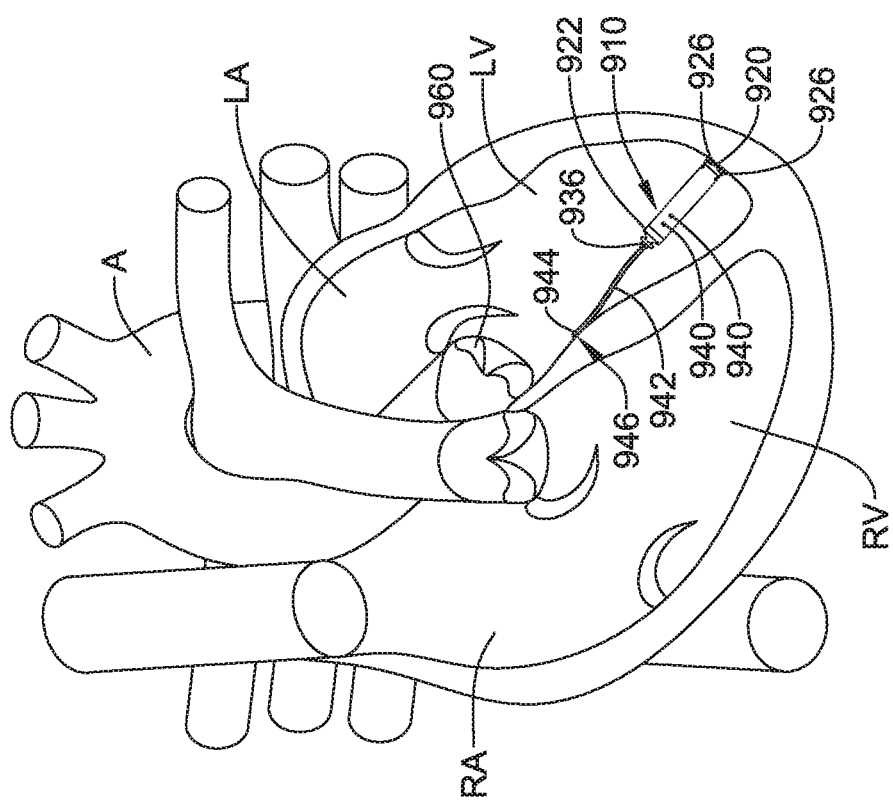
FIG. 10A is a plan view of the example leadless cardiac pacing device of FIG. 8 implanted within a heart in a first configuration.
Figure 10B:
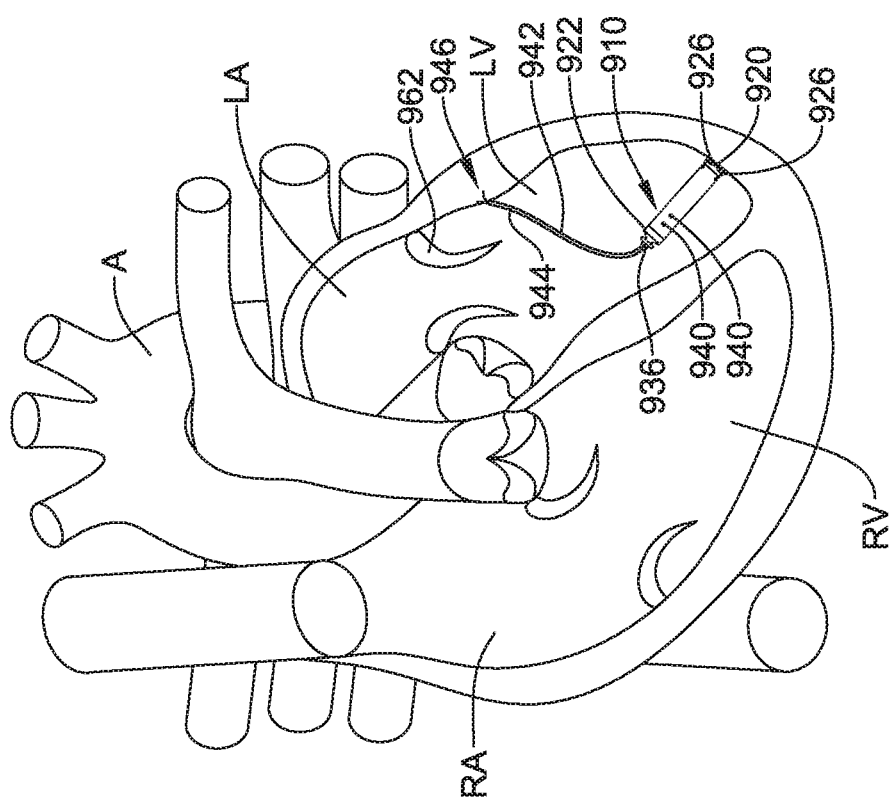
FIG. 10B is a plan view of the example leadless cardiac pacing device of FIG. 8 implanted within a heart in a second configuration.

FIGS. 10A-10C are plan views of the example leadless cardiac pacing device 910 implanted within a left ventricle LV of the heart H. The right ventricle RV, right atrium RA, left atrium LA, and aorta A are also illustrated. The LCP 910 may be affixed within the left ventricle LV such that the first electrode 920 is generally positioned in an apex of the left ventricle LV as shown. However this is not required, and it is contemplated that the first electrode 920 may be positioned and secured anywhere within the left ventricle LV, as desired. In FIG. 10A, the proximal end region 948 of the tail 942 is positioned adjacent to the aortic valve 960 and still within the left ventricle. In FIG. 10B, the proximal end region 948 of the tail 942 is positioned adjacent to the mitral valve 962 and still within the left ventricle. In FIG. 10C, the proximal end region 948 of the tail 942 is positioned adjacent to and/or within the left atrium LA of the heart H. It is contemplated that placing one of the electrodes 944 of the tail 942 in the left atrium LA may allow the LCP 910 to directly measure electrical signals of the left atrium LA (e.g. the P-wave). In some cases, maximizing the distance between the electrode 944 of the tail 942 and the first and/or second electrodes 920, 922 may provide a more accurate impedance measurement because more of the electrical current may pass through the blood in the chamber and less through the muscular tissue of the heart H. In any of the configurations illustrated in FIGS. 10A-10C, the fixation mechanism 946, if so provided, may be used to secure the tail 942 to the heart H at the corresponding fixation location. It is contemplated that the tail 942 may be fixed at a fixation location where the impedance data obtained is most sensitive to volume change in the chamber (LV). Alternatively, or additionally, tail 942 may be fixed at a fixation location in the left atrium that achieves a good signal-to-noise ratio of electrical signals related to atrium activity (e.g. P-wave). In some cases, the tail may have one or more electrodes positioned in the atrium for sensing electrical activity of the atrium, and one or more electrodes in the ventricle for sensing the impedance and thus the volume of the ventricle. In some embodiments, the tail 942 may not be fixed at the proximal end 948. The configurations illustrated in FIGS. 10A-10C are not intended to be limiting but rather are intended to illustrative several configurations of the housing with the tail 942 when implanted in the heart H. In some cases, the LCP 910 may be placed in the right ventricle (RV). In some cases, an LCP 910 may be placed in each of the RV and LV of the heart H.

In some cases, the processing module and/or other control circuitry of the LCP 910 may capture, at a time point within each of one or more cardiac cycles, an impedance between at least one pair of electrodes. The impedance may be used as a surrogate for blood volume in the heart. Monitoring a derivative (e.g. slope) of the volume (e.g. dV/dt) over a cardiac cycle may allow for the determination of the volume of blood entering the left ventricle that is associated with passive filling, and a volume of blood entering the left ventricle that is associated with an atrial contraction (e.g. atrial kick). The change in rate of volume filling, and timing of such change in rate of volume filling, may help identify an atrial fiducial associated with an atrium contraction. The atrial fiducial may then be used to time a pacing pulse for the ventricle in support of cardiac resynchronization therapy (CRT). For example, the timing of the ventricle pacing pulse may be adjusted to maximize the amount of blood entering the left ventricle through passive filling. In another example, the timing of the ventricle pacing pulse may be adjusted to maximize the dP/dt (slope of pressure versus time). These are just some examples. In some instances, this may include adjusting the AV delay relative to the atrial fiducial. In some cases, the measured impedance, and corresponding chamber volume, may be used to support management of a non-CRT cardiac therapy, patient health status monitoring and/or any other suitable goal. In some cases, the impedance data may be combined with additional sensor data (e.g. electrical, pressure, acoustic, acceleration, chemical, optical) to support management of CRT or a non-CRT therapy.

While an LCP may be used to collect the impedance data as described above, it is contemplated that a diagnostic device that has no pacing capabilities may be used to collect the impedance and/or other data (e.g. pressure data). The diagnostic device may include two or more electrodes for measuring an impedance and/or for communicating with an LCP, S-ICD, or other device. The diagnostic device may be implanted with a chamber of the heart H. In some cases, a diagnostic device and LCP, both implanted in the same chamber, may cooperate to collect the impedance and/or other data. As described above, the impedance may be correlated to blood volume in a chamber thus the volume of the chamber.

Figure 11:
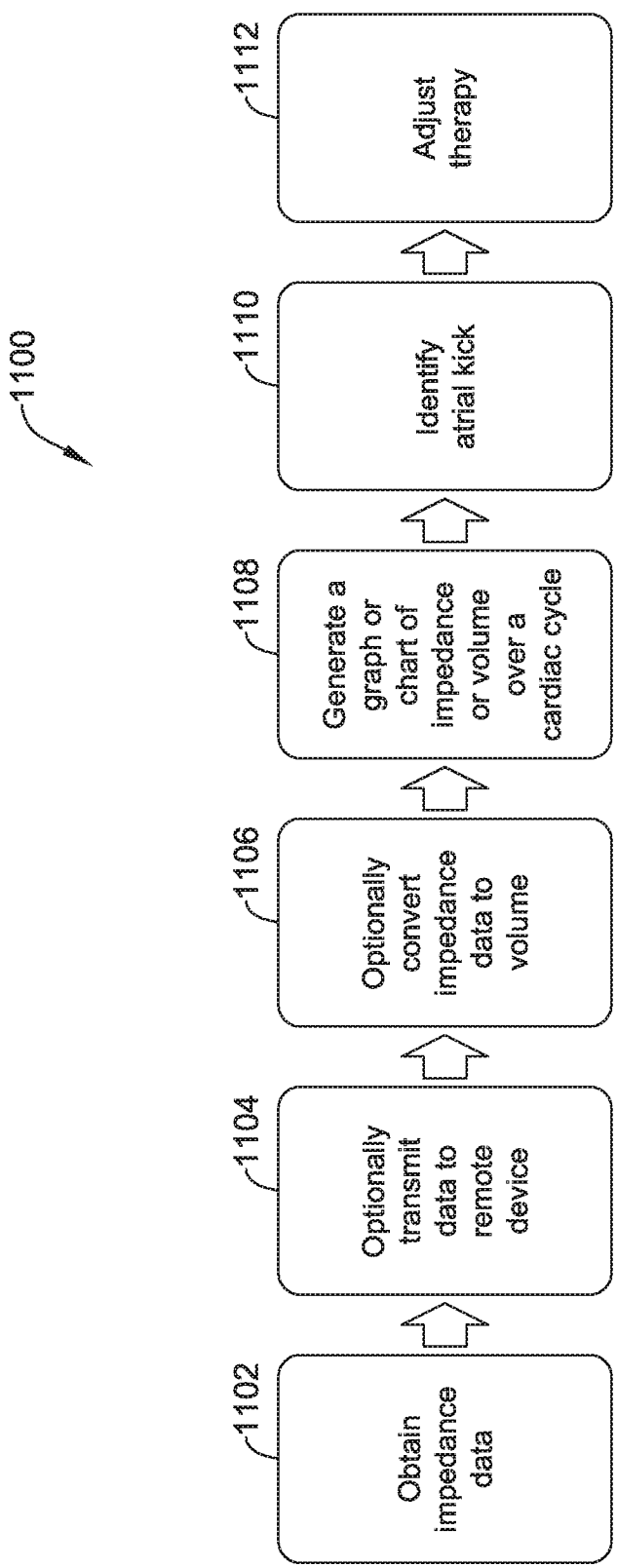
FIG. 11 is a flow diagram of an illustrative method for adjusting a Cardiac Resynchronization Therapy (CRT).

FIG. 11 is a flow chart of an illustrative method 1100 for generating a graph or chart of impedance and/or volume from data obtained from an implanted LCP such as any of the above described LCP devices 100, 302, 304, 402, 502, 610, 910. While the method is described using an LCP, it is contemplated that other devices and/or combinations of devices may be used. For example, two or more LCPs may be used to collect data from different chambers in the heart (e.g. RV and LV, RA and RV, LA and LV). As described above, the LCP may include a processing module that includes control circuitry configured to control the operation of the LCP. In some instances, the processing module may include separate circuits for therapy delivery, hemodynamic (e.g. pressure) sensing, and/or volume sensing, although this is not required. It is contemplated that the processing module may further include an additional circuit or algorithm for generating a volume graph or chart which may be configured to convert the impedance data obtained from the two or more electrodes into a heart chamber volume graph (e.g. a graph illustrating the volume of a heart chamber versus time over one or more cardiac cycles).

As shown at block 1102, the processing module of one or more LCPs (and/or other implantable devices) may obtain an impedance measurement at a first time during a cardiac cycle, resulting in a first impedance data point. In some instances, the first time may correspond with an S1 heart sound, although this is not required. The data point may be stored in a memory of the LCP. In some instances, the data point may be stored in a table. In some cases, the data point may be transmitted to a remote device, such as another LCP, an S-ICD device, or an external device. The processing module may then obtain one or more additional impedance data points at different times during the same cardiac cycle. For example, a second impedance data point may be determined at a second time, a third impedance data point may be determined at a third time, a fourth impedance data point may be determined at a fourth time, etc. In some instances, the second time may correspond with an S2 heart sound, although this is not required. The one or more additional data points may be stored in the memory of the LCP. In some cases, the LCP may transmit the impedance data points to another device, such as an S-ICD device or a remote or external device, as shown at block 1104. However, this is not required. When the impedance data is processed by a remote device, the LCP circuitry may be configured to receive processed information from the remote device. In some instances, the LCP may be provided with the circuitry and processing capabilities to process and analyze the impedance data, or parts thereof.

It is contemplated that the processing module may be configured to sample impedance data points at set time intervals or to obtain a predetermined number of impedance data points per cardiac cycle. It is contemplated that increasing the frequency of sampling may result in a more accurate and/or higher resolution chamber volume chart. However, frequent sampling may decrease the life of the battery of the LCP(s). Moreover, the use of the terms "first time" and "second time" are not intended to chronologically limit the order the impedance data points are obtained. In some instances, the circuitry may be configured to determine, at a plurality of times between the first time and the second time, a plurality of corresponding impedances between a first electrode and a second electrode (or other electrode combinations or multiple electrode pairs), resulting in a plurality of additional impedance data points. In some cases, the plurality of times may include at least one time corresponding to an end-systolic time point and at least one time corresponding to an end-diastolic time point. A difference of an impedance determined at the end diastolic time point and an impedance determined at the end-systolic time point may be a measure of a stroke volume of the ventricle in which the LCP is implanted. In some instances, the circuitry may be configured to change the sampling frequency during the cardiac cycle such that more frequent samples are gathered during times when the impedance is rapidly changing such as, but not limited to, during contraction of the ventricles.

Once the LCP has gathered impedance data pairs over at least one cardiac cycle, the LCP and/or external device may convert the impedance data into corresponding chamber volumes, as shown at block 1106. However, this is not required. The LCP and/or the external device may use the impedance data as a surrogate for the chamber volume. The LCP and/or external device may generate an impedance versus time or a volume versus time graph or equivalent, as shown at block 1108. For example, the LCP or an external device may be configured to generate a volume graph that is based, at least in part, on the plurality of data points. In some embodiments, the processing module and/or external device may be configured to generate an impedance graph instead of a volume graph. The impedance graph may provide similar information as the volume graph but may require less processing. At a high level, the impedance graph may be considered equivalent to the volume graph.

It is contemplated that data points obtained over a plurality (e.g. two or more, five or more, ten or more) of cardiac cycles may be averaged before generating the volume graph. For example, the LCP circuitry may be configured to record or sample impedance data at the same (or similar) time points in each in a series of cardiac cycles such that the first impedance data point from a first cardiac cycle can be averaged with the corresponding first impedance data point from any number of subsequent (or preceding) cardiac cycles. Averaging the data over a plurality of cardiac cycles may reduce the noise and provide a more robust representation of the chamber volume versus time.

In some embodiments, multiple impedance data points may be obtained from multiple electrode vectors (e.g. multiple electrode pairs) simultaneously, or substantially simultaneously. In some instances, the LCP circuitry may be configured to select the best electrode vector. In other instances, the LCP circuitry may be configured to generate multiple volume graphs based on the data obtained from the multiple electrode vectors. This may allow the circuitry to, for example, better separate ventricular and atrial contraction components.

In some instances, the processing module may include circuitry to convert the data pairs into a chamber volume graph, as shown at block 1106. In other instances, the LCP circuitry may be configured to wirelessly transmit the first impedance data point (and/or any additional data points) to a remote or external device, such as, but not limited to, any of the medical or external devices described above, as shown at block 1104. The LCP may communicate with the remote or external device via radiofrequency (RF) signals, inductive coupling, optical signals, acoustic signals, conducted communication signals, and/or any other signals suitable for communication. In some cases, the remote device may be configured to display the data and/or processed data on a screen for a clinician to view.

Various metrics may be extracted from the chamber volume graph, as desired, as shown at block 1110. For example, the chamber volume graph may be used to identify a contraction of the atrium (e.g. the atrial kick, which may be used to produce an atrial fiducial) and/or the end diastolic volume of the left ventricle. This may allow the LCP circuitry (and/or external device) to determine the percentage of ventricular filling attributed to passive filling and the percentage of ventricular filling attributed to atrial contraction. The LCP circuitry may be configured to identify the atrial kick (e.g. change in passive ventricular filling to active ventricular filling) in a number of different ways. For example, the LCP circuitry may be configured to identify a change in derivative (e.g. a change in slope) of the volume versus time. In other words, the change in volume with respect to time may increase at the atrial kick. Additionally, or alternatively, the LCP circuitry may be configured to identify a change in volume during the later portion of diastole, which could be attributed to the atrial kick. Additionally, or alternatively, the S4 heart sound may be indicative of the atrial kick. It is contemplated that a marker or annotation may be used to denote the impedance data point that most closely aligns with the S4 heart sound. Additionally, or alternatively, the electrodes on the LCP and/or the tail may directly measure the electrical activity of the atrium, and may directly identify the P-wave of the ECG. It is contemplated that a marker or annotation may be used to denote the impedance data point that most closely aligns with the A wave.

As heart failure progresses, the percentage of ventricular filling attributed to atrial contraction increases. As such, the change in volume due to the atrial kick may depend on the health (e.g. heart failure status) of the patient. Knowing this percentage may provide a clinician with a metric related to the patient's heart failure status. In some cases, the volume graph may be used to determine an ejection fraction (e.g. stroke volume/peak volume) of the cardiac cycle. Other heart metrics may also be determined.

It is contemplated that the LCP circuitry and/or external device circuitry may be configured to adjust the therapy based on the metrics obtained from the ventricular volume graph, as shown at block 1112. It is contemplated that the volume graph and/or the extracted metrics may be used to improve therapies and/or provide the clinician with information regarding cardiac functionality. For example, the volume graph and/or extracted metrics may be used to change the AV delay when pacing, the electrodes used for pacing and/or sensing, pacing timing, and/or optimization of CRT and non-CRT therapies, etc. In some cases, it is contemplated that when the volume graph is generated within the processing module of the LCP, and the processing module may be programmed to improve CRT therapies with or without a clinician viewing the volume data.

In one example, the atrial kick may provide an atrial fiducial. The timing of the ventricle pacing pulse may be based at least in part on the atrial fiducial, such as after an AV delay following the atrial fiducial. In some cases, the LCP circuitry and/or external device circuitry may be configured to modify the AV delay, one or more pacing sites, a pacing site sequence (e.g. RV-LV or LV-RV) or a ventricular-to-ventricular delay (VV delay) to optimize the ejection fraction (e.g. to achieve the largest ejection fraction). It is contemplated that the absolute volume of the impedance may be maximized (e.g. minimize ventricular volume) at the end of the stroke (e.g. end of systole) to maximize the ejection fraction. In some instances, the LCP circuitry and/or external device circuitry may be configured to modify a therapy to achieve a largest ratio of stroke volume to a peak volume. In other cases, the LCP circuitry and/or external device circuitry may be configured to pace until the ratio of active filling to passive filling is minimized (e.g. to maximize passive filling).

In some embodiments, the LCP may be configured to obtain pressure data points at substantially the same time as the impedance data points, as described in commonly assigned application (Atty Docket No. 2001.1332100), filed on even date herewith, which is hereby incorporated by reference. The pressure data may be combined with the impedance data to generate a pressure-volume loop (or pressure-impedance loop) which may provide additional metrics to further improve the CRT and/or non-CRT therapies. For example, the loop area and loop width may be determined from the pressure-volume loop. A measure of the contractility index of the heart can be estimated by calculating the slope of the end systolic pressure-volume line. A measure of the stroke work can be estimated by the area of the loop. A measure of the stroke volume can be estimated by the End Diastole-Volume (EDV) minus the End Systole-Volume (EDV) of the loop. A measure of the ejection fraction can be estimated by the stroke volume divided by the EDV. These are only illustrative, and it is contemplated that other metrics may also be extracted or derived from the pressure-volume loop.

In some instances, the LCP may be in wireless communication with an external wearable device, such as an activity tracker (e.g. iWatch®, FitBit®, etc.), that may provide contextual information such as sleep status and/or activity level of the patient. It is contemplated that the generated PV loops may be processed or grouped according to context. For example, PV loops may be processed according to time of day, posture, activity level, metabolic demands, heart rate range, sleep state, etc.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A method for detecting an atrial fiducial using a leadless cardiac pacemaker (LCP) that is implanted in a particular ventricle of a patient's heart, wherein the LCP has first electrode and a second electrode spaced from the first electrode with both the first electrode and the second electrode configured to be positioned in the particular ventricle of the patient's heart, the method comprising:
   identifying a measure of impedance between the first electrode and the second electrode of the LCP at each of a plurality of times during a cardiac cycle of the patient's heart, wherein each measure of impedance represents a measure of volume of the particular ventricle in which the LCP is implanted;
   determining the atrial fiducial based on the measure of volume of the particular ventricle at two or more of the plurality of times during the cardiac cycle; and
   generating a pacing pulse during the cardiac cycle, the timing of which is based at least in part on the determined atrial fiducial.

2. The method of claim 1, wherein the atrial fiducial corresponds to a contraction of the atrium of the patient's heart.

3. The method of claim 1, further comprising generating the pacing pulse after an AV delay following the determined atrial fiducial.

4. The method of claim 3, further comprising controlling the AV delay to increase a peak derivative of the volume of the particular ventricle.

5. The method of claim 1, wherein the LCP includes a tail comprising two or more electrodes, and the method further comprises selecting one of the two or more electrodes of the tail as the second electrode.

6. The method of claim 1, wherein the LCP includes a housing having three or more electrodes, and the method further comprises selecting one of the three or more electrodes as the second electrode.

7. The method of claim 1, wherein the LCP further includes a third electrode and a fourth electrode, and the method further comprises:
   applying an impedance current between the third electrode and the fourth electrode; and
   sensing an impedance voltage between the first electrode and the second electrode to identify the measure of impedance between the first electrode and the second electrode.

8. The method of claim 1, further comprising:
   applying an impedance current by a remote device; and
   sensing a voltage between the first electrode and the second electrode to identify the measure of impedance between the first electrode and the second electrode.

9. The method of claim 1, further comprising wirelessly communicating the measures of impedance between the first electrode and the second electrode at the plurality of times during the cardiac cycle to a remote device.

10. The method of claim 9, further comprising receiving processed information from the remote device that is a result of the remote device processing the measures of impedance between the first electrode and the second electrode at the plurality of times during the cardiac cycle.

11. The method of claim 10, wherein the timing of the pacing pulse is based at least in part on the processed information from the remote device.

12. The method of claim 1, further comprising:
   storing the measures of impedance between the first electrode and the second electrode at the plurality of times during the cardiac cycle in a memory; and
   determining the atrial fiducial based at least in part on the measures of volume of the particular ventricle at two or more of the plurality of times during the cardiac cycle.

13. The method of claim 1, further comprising sensing one or more electrical signals of the patient's heart;
   wherein determining the atrial fiducial is based on:
   the measure of volume of the particular ventricle at two or more of the plurality of times during the cardiac cycle; and
   the one or more sensed electrical signals of the patient's heart.

14. The method of claim 1, further comprising sensing one or more heart sound signals;
   wherein determining the atrial fiducial is based on:
   the measure of volume of the particular ventricle at two or more of the plurality of times during the cardiac cycle; and
   the one or more sensed heart sound signals.

15. The method of claim 1, further comprising sensing one or more pressure signals representative of a pressure in the particular ventricle of the patient's heart;
   wherein determining the atrial fiducial is based on:
   the measure of volume of the particular ventricle at two or more of the plurality of times during the cardiac cycle; and
   the one or more pressure signals representative of the pressure in the particular ventricle of the patient's heart.

16. The method of claim 1, further comprising identifying a change from a passive filling to an active filling of the particular ventricle in which the LCP is implanted by detecting a change in slope in the plurality of impedances.

17. The method of claim 1, wherein the plurality of times includes at least one time corresponding to an end-systolic time of the cardiac cycle and at least one time corresponding to an end-diastolic time point of the cardiac cycle, and wherein a difference of an impedance determined at the end-diastolic time point and an impedance determined at the end-systolic time point indicates a measure of a stroke volume of the particular ventricle in which the LCP is implanted.

18. The method of claim 1, further comprising:
   determining one or more metrics of the patient's heart based at least in part on the measure of volume of the particular ventricle at two or more of the plurality of times during the cardiac cycle; and
   determining the atrial fiducial based at least in part on the one or more metrics.

19. The method of claim 18, wherein the one or more metrics comprise a percentage of ventricular filling attributed to passive filling and/or a percentage of ventricular filling attributed to atrial contraction.

20. The method of claim 18, wherein the one or more metrics comprise an ejection fraction of the particular ventricle of a patient's heart.

* * * * *